US007763616B2

United States Patent
Yu et al.

(10) Patent No.: US 7,763,616 B2
(45) Date of Patent: Jul. 27, 2010

(54) PIPERAZINE-PIPERIDINES WITH CXCR3 ANTAGONIST ACTIVITY

(75) Inventors: Wensheng Yu, Edison, NJ (US); Seong Heon Kim, Livingston, NJ (US); Gopinadhan N. Anilkumar, Edison, NJ (US); Stuart B. Rosenblum, West Orange, NJ (US); Bandarpalle B. Shankar, Branchburg, NJ (US); Brian F. McGuinness, Plainsboro, NJ (US); Douglas W. Hobbs, Yardley, PA (US); Yuefei Shao, Princeton, NJ (US)

(73) Assignee: Schering Corporation, Kenilworth, NJ (US)

( * ) Notice: Subject to any disclaimer, the term of this patent is extended or adjusted under 35 U.S.C. 154(b) by 414 days.

(21) Appl. No.: 11/353,806

(22) Filed: Feb. 14, 2006

(65) Prior Publication Data

US 2006/0276457 A1    Dec. 7, 2006

Related U.S. Application Data

(60) Provisional application No. 60/653,378, filed on Feb. 16, 2005.

(51) Int. Cl.
| | |
|---|---|
| A61K 31/5025 | (2006.01) |
| A61K 31/4985 | (2006.01) |
| C07D 245/02 | (2006.01) |
| C07D 255/02 | (2006.01) |
| C07D 257/08 | (2006.01) |
| C07D 259/00 | (2006.01) |
| C07D 239/04 | (2006.01) |
| C07D 239/70 | (2006.01) |
| C07D 471/04 | (2006.01) |
| C07D 487/04 | (2006.01) |
| A61K 31/497 | (2006.01) |
| C07D 241/36 | (2006.01) |
| C07D 401/14 | (2006.01) |
| C07D 403/14 | (2006.01) |
| C07D 405/14 | (2006.01) |
| C07D 409/14 | (2006.01) |
| A61P 29/00 | (2006.01) |
| A61P 17/06 | (2006.01) |
| A61P 19/02 | (2006.01) |
| A61P 3/10 | (2006.01) |
| A61P 31/08 | (2006.01) |

(52) U.S. Cl. ............... 514/249; 540/460; 540/502; 540/557; 544/350; 544/258; 544/357; 544/229; 544/393; 544/360; 544/364; 544/354; 514/253.01; 514/183; 514/221; 514/220; 514/253.09

(58) Field of Classification Search ........... 514/249, 514/183, 221, 220; 540/460, 501, 502, 557; 544/350, 249, 258

See application file for complete search history.

(56) References Cited

U.S. PATENT DOCUMENTS

| 6,124,319 A | 9/2000 | MacCoss et al. |
|---|---|---|
| 7,417,045 B2 | 8/2008 | Anilkumar et al. |
| 7,566,718 B2 | 7/2009 | Wong et al. |

(Continued)

FOREIGN PATENT DOCUMENTS

| WO | WO93/10091 | 5/1993 |
|---|---|---|
| WO | WO 93/14077 | 7/1993 |
| WO | WO99/20606 | 4/1999 |
| WO | WO 00/66558 | 11/2000 |
| WO | WO02/085861 | 10/2002 |

(Continued)

OTHER PUBLICATIONS

International Search Report for International Application No. PCT/US2006/005121 mailed Aug. 4, 2006—3 pgs.
Qingbei Zeng et al., U.S. Appl. No. 12/519,970; Preliminary Amendment —Mailed Jun. 18, 2009.

*Primary Examiner*—Mark L Berch
*Assistant Examiner*—Cecilia M Jaisle
(74) *Attorney, Agent, or Firm*—Palaiyur S. Kalyanaraman; Krishna G. Banerjee

(57) ABSTRACT

The present application discloses a compound, or enantiomers, stereoisomers, rotamers, tautomers, racemates or prodrug of said compound, or pharmaceutically acceptable salts, solvates or esters of said compound, or of said prodrug, said compound having the general structure shown in Formula 1:

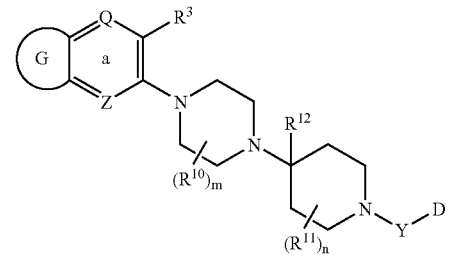

Formula 1 or a pharmaceutically acceptable salt, solvate or ester thereof, wherein the various moieties are defined herein. Also disclosed is a method of treating chemokine mediated diseases, such as, palliative therapy, curative therapy, prophylactic therapy of certain diseases and conditions such as inflammatory diseases (non-limiting example(s) include, psoriasis), autoimmune diseases (non-limiting example(s) include, rheumatoid arthritis, multiple sclerosis), graft rejection (non-limiting example(s) include, allograft rejection, xenograft rejection), infectious diseases (e.g, tuberculoid leprosy), fixed drug eruptions, cutaneous delayed-type hypersensitivity responses, ophthalmic inflammation, type I diabetes, viral meningitis and tumors using a compound of Formula 1.

7 Claims, No Drawings

U.S. PATENT DOCUMENTS

| | | |
|---|---|---|
| 2002/0018776 A1 | 2/2002 | Hancock |
| 2003/0055054 A1 | 3/2003 | Medina et al. |
| 2006/0276448 A1 | 12/2006 | Zeng et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2008/0039474 A1 | 2/2008 | Rosenblum et al. |
| 2008/0058343 A1 | 3/2008 | Rosenblum et al. |
| 2008/0292589 A1 | 11/2008 | Anilkumar et al. |

FOREIGN PATENT DOCUMENTS

| | | |
|---|---|---|
| WO | WO03/070242 | 8/2003 |
| WO | WO03/082335 | 10/2003 |
| WO | WO03/098185 | 11/2003 |
| WO | WO03/101970 | 12/2003 |
| WO | WO2008/079279 | 7/2008 |

PIPERAZINE-PIPERIDINES WITH CXCR3 ANTAGONIST ACTIVITY

REFERENCE TO PRIORITY APPLICATIONS

This application claims the benefit of U.S. Provisional Application Ser. No. 60/653,378 filed on Feb. 16, 2005, which is incorporated herein in its entirety by reference.

FIELD OF THE INVENTION

The present invention relates to novel pyridyl and phenyl substituted piperazine-piperidines with CXCR3 antagonist activity, pharmaceutical compositions containing one or more such antagonists, one or more such antagonists in combination with other compounds with chemokine activity, one or more such antagonists in combination with known immunosuppressive agents, non-limiting example(s) include Methotrexate, interferon, cyclosporin, FK-506 and FTY720, methods of preparing such antagonists and methods of using such antagonists to modulate CXCR3 activity. This invention also discloses methods of using such CXCR3 antagonists for the treatment (non-limiting examples include palliative, curative and prophylactic therapies) of diseases and conditions where CXCR3 has been implicated. Diseases and conditions where CXCR3 has been implicated include but are not limited to inflammatory conditions (psoriasis and inflammatory bowel disease), autoimmune disease (multiple sclerosis, rheumatoid arthritis), fixed drug eruptions, cutaneous delayed-type hypersensitivity responses, type I diabetes, viral meningitis and tuberculoid leprosy. CXCR3 antagonist activity has also been indicated as a therapy for tumor growth suppression as well as graft rejection (allograft and zenograft rejections for example).

BACKGROUND OF THE INVENTION

Chemokines constitute a family of small cytokines that are produced in inflammation and regulate leukocyte recruitment (Baggiolini, M. et al., *Adv. Immunol.*, 55: 97-179 (1994); Springer, T. A., *Annu. Rev. Physio.*, 57: 827-872 (1995); and Schall, T. J. and K. B. Bacon, *Curr. Opin. Immunol*, 6: 865-873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

The chemokines are related in primary structure and share four conserved cysteines, which form disulfide bonds. Based upon this conserved cysteine motif, the family can be divided into distinct branches, including the C—X—C chemokines (α-chemokines) in which the first two conserved cysteines are separated by an intervening residue (e.g., IL-8, IP-10, Mig, I-TAC, PF4, ENA-78, GCP-2, GROα, GROβ, GROδ, NAP-2, NAP-4), and the C—C chemokines (β-chemokines), in which the first two conserved cysteines are adjacent residues (e.g., MIP-1α, MIP-1β, RANTES, MCP-1, MCP-2, MCP-3, I-309) (Baggiolini, M. and Dahinden, C. A., *Immunology Today*, 15:127-133 (1994)). Most CXC-chemokines attract neutrophil leukocytes. For example, the CXC-chemokines interleukin 8 (IL-8), GRO alpha (GROα), and neutrophil-activating peptide 2 (NAP-2) are potent chemoattractants and activators of neutrophils. The CXC-chemokines designated Mig (monokine induced by gamma interferon) and IP-10 (interferon-gamma inducible 10 kDa protein) are particularly active in inducing chemotaxis of activated peripheral blood lymphocytes. CC-chemokines are generally less selective and can attract a variety of leukocyte cell types, including monocytes, eosinophils, basophils, T lymphocytes and natural killer cells. CC-chemokines such as human monocyte chemotactic proteins 1-3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

A chemokine receptor that binds the CXC-chemokines IP-10 and Mig has been cloned and characterized (Loetscher, M. et al., *J. Exp. Med.*, 184: 963-969 (1996)). CXCR3 is a G-protein coupled receptor with seven transmembrane-spanning domains and has been shown to be restrictively expressed in activated T cells, preferentially human Th1 cells. On binding of the appropriate ligand, chemokine receptors transduce an intracellular signal through the associated G-protein resulting in a rapid increase in intracellular calcium concentration.

The receptor mediates $Ca^{2+}$ (calcium ion) mobilization and chemotaxis in response to IP-10 and Mig. CXCR3 expressing cells show no significant response to the CXC-chemokines IL-8, GROα, NAP-2, GCP-2 (granulocyte chemotactic protein-2), ENA78 (epithelial-derived neutrophil-activating peptide 78), PF4 (platelet factor 4), or the CC-chemokines MCP-1, MCP-2, MCP-3, MCP-4, MIP-1α, MIP-1β, RANTES, I309, eotaxin or lymphotactin. Moreover, a third ligand for CXCR3, I-TAC (Interferon-inducible T cell Alpha Chemoattractant), has also been found to bind to the receptor with high affinity and mediate functional responses (Cole, K. E. et al., *J. Exp. Med.*, 187: 2009-2021 (1998)).

The restricted expression of human CXCR3 in activated T lymphocytes and the ligand selectivity of CXCR3 are noteworthy. The human receptor is highly expressed in IL-2 activated T lymphocytes, but was not detected in resting T lymphocytes, monocytes or granulocytes (Qin, S. et al., *J. Clin. Invest.*, 101: 746-754 (1998)). Additional studies of receptor distribution indicate that it is mostly $CD3^+$ cells that express CXCR3, including cells which are $CD95^+$, $CD45RO^+$, and $CD45RA^{low}$, a phenotype consistent with previous activation, although a proportion of $CD20^+$ (B) cells and $CD56^+$ (NK) cells also express this receptor. The selective expression in activated T lymphocytes is of interest, because other receptors for chemokines which have been reported to attract lymphocytes (e.g., MCP-1, MCP-2, MCP-3, MIP-1α, MIP-1β, RANTES) are also expressed by granulocytes, such as neutrophils, eosinophils, and basophils, as well as monocytes. These results suggest that the CXCR3 receptor is involved in the selective recruitment of effector T cells.

CXCR3 recognizes unusual CXC-chemokines, designated IP-10, Mig and I-TAC. Although these belong to the CXC-subfamily, in contrast to IL-8 and other CXC-chemokines which are potent chemoattractants for neutrophils, the primary targets of IP-10, Mig and I-TAC are lymphocytes, particularly effector cells such as activated or stimulated T lymphocytes and natural killer (NK) cells (Taub, D. D. et al., *J*

Exp. Med., 177: 18090-1814 (1993); Taub, D. D. et al., *J. Immunol.*, 155: 3877-3888 (1995); Cole, K. E. et al., *J. Exp. Med.*, 187: 2009-2021 (1998)). (NK cells are large granular lymphocytes, which lack a specific T cell receptor for antigen recognition, but possess cytolytic activity against cells such as tumor cells and virally infected cells.) Consistently, IP-10, Mig and I-TAC lack the ELR motif, an essential binding epitope in those CXC-chemokines that efficiently induce neutrophil chemotaxis (Clark-Lewis, I. et al., *J. Biol. Chem.* 266: 23128-23134 (1991); Hebert, C. A. et al., *J. Biol. Chem.*, 266: 18989-18994 (1991); and Clark-Lewis, 1. et al., *Proc. Natl. Acad. Sci. USA*, 90: 3574-3577 (1993)). In addition, both recombinant human Mig and recombinant human IP-10 have been reported to induce calcium flux in tumor infiltrating lymphocytes (TIL) (Liao, F. et al., *J Exp. Med*, 182: 1301-1314 (1995)). While IP-10 has been reported to induce chemotaxis of monocytes in vitro (Taub, D. D. et al., *J. Exp. Med.*, 177: 1809-1814 (1993), the receptor responsible has not been identified), human Mig and I-TAC appear highly selective, and do not show such an effect (Liao, F. et al., *J. Exp. Med.*, 182: 1301-1314 (1995); Cole, K. E. et al., *J. Exp. Med.*, 187: 2009-2021 (1998)). IP-10 expression is induced in a variety of tissues in inflammatory conditions such as psoriasis, fixed drug eruptions, cutaneous delayed-type hypersensitivity responses and tuberculoid leprosy as well as tumors and in animal model studies, for example, experimental glomerulonephritis, and experimental allergic encephalomyelitis. IP-10 has a potent in vivo antitumor effect that is T cell dependent, is reported to be an inhibitor of angiogenesis in vivo and can induce chemotaxis and degranulation of NK cells in vitro, suggesting a role as a mediator of NK cell recruitment and degranulation (in tumor cell destruction, for example) (Luster, A. D. and P. Leder, *J. Exp. Med.*, 178: 1057-1065 (1993); Luster, A. D. et al., *J. Exp. Med.* 182: 219-231 (1995); Angiolillo, A. L. et al., *J. Exp. Med.*, 182: 155-162 (1995); Taub, D. D. et al., *J. Immunol.*, 155: 3877-3888 (1995)). The expression patterns of IP-10, Mig and I-TAC are also distinct from that of other CXC chemokines in that expression of each is induced by interferon-gamma (IFNδ), while the expression of IL-8 is down-regulated by IFNδ (Luster, A. D. et al., *Nature*, 315: 672-676 (1985); Farber, J. M., *Proc. Natl. Acad. Sci. USA*, 87: 5238-5242 (1990); Farber, J. M., *Biochem. Biophys. Res. Commun.*, 192 (1): 223-230 (1993), Liao, F. et al., *J. Exp. Med.*, 182: 1301-1314 (1995); Seitz, M. et al., *J. Clin. Invest.*, 87: 463-469 (1991); Galy, A. H. M. and H. Spits, *J. Immunol.*, 147: 3823-3830 (1991); Cole, K. E. et al., *J. Exp. Med.*, 187: 2009-2021 (1998)).

Chemokines are recognized as the long-sought mediators for the recruitment of lymphocytes. Several CC-chemokines were found to elicit lymphocyte chemotaxis (Loetscher, P. et al., *FASEB J.*, 8: 1055-1060 (1994)), however, they are also active on granulocytes and monocytes (Uguccioni, M. et al., *Eur. J. Immunol.*, 25: 64-68 (1995); Baggiolini, M. and C. A. Dahinden, *Immunol. Today*, 15: 127-133 (1994)). The situation is different for IP-10, Mig and I-TAC, which are selective in their action on lymphocytes, including activated T lymphocytes and NK cells, and which bind CXCR3, a receptor which does not recognize numerous other chemokines and which displays a selective pattern of expression.

In view of these observations, it is reasonable to conclude that the formation of the characteristic infiltrates in inflammatory lesions, such as, for example, delayed-type hypersensitivity lesions, sites of viral infection and certain tumors is a process mediated via CXCR3 and regulated by CXCR3 expression. Lymphocytes, particularly T lymphocytes, bearing a CXCR3 receptor as a result of activation can be recruited into inflammatory lesions, sites of infection and/or tumors by IP-10, Mig and/or I-TAC, which can be induced locally by interferon-gamma. Thus, CXCR3 plays a role in the selective recruitment of lymphocytes, particularly effector cells such as activated or stimulated T lymphocytes. Accordingly, activated and effector T cells have been implicated in a number of disease states such as graft-rejection, inflammation, rheumatoid arthritis, multiple sclerosis, inflammatory bowel disease (such as Crohn's disease and ulcerative colitis) and psoriasis. Thus, CXCR3 represents a promising target for the development of novel therapeutics.

Reference is made to PCT Publication No. WO 93/10091 (Applicant: Glaxo Group Limited, Published May 27, 1993) which discloses piperidine acetic acid derivatives as inhibitors of fibrinogen-dependent blood platelet aggregation having the formula:

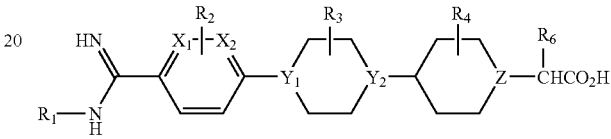

An illustrative compound of that series is:

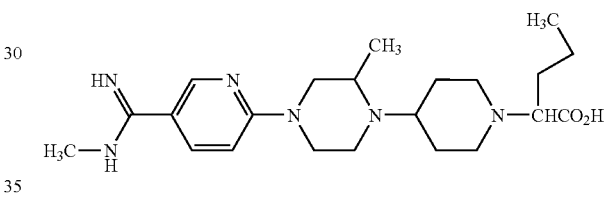

Reference is also made to PCT Publication No. WO 9/20606 (Applicant: J. Uriach & CIA. S. A., Published Apr. 29, 1999) which discloses piperazines as platelet aggregation inhibitors having the formula:

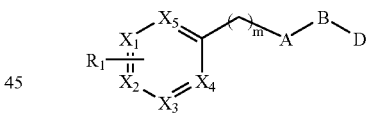

Reference is also made to US Patent Application No. US 2002/0018776 A1 (Applicant: Hancock, et al. Published Feb. 14, 2002) which discloses methods of treating graft rejection.

Reference is also made to PCT Publication No. WO 03/098185 A2 (Applicant: Renovar, Inc., Published Nov. 27, 2003) which discloses methods of diagnosing and predicting organ transplant rejection by detection of chemokines, for example, CXCR3 and CCL chemokines in urine.

Reference is also made to PCT Publication No. WO 03/082335 A1 (Applicant: Sumitomo Pharmaceuticals Co. Ltd., Published Oct. 9, 2003) which discloses methods of screening a CXCR3 ligand and methods of diagnosing type 2 diabetes by detecting the expression dose of a CXCR3 ligand in a biological sample.

Reference is also made to PCT Publication No. WO 02/085861 (Applicant: Millennium Pharmaceuticals, Inc. Published Oct. 31, 2002) which discloses imidazolidine compounds and their use as CXCR3 antagonists having the formula:

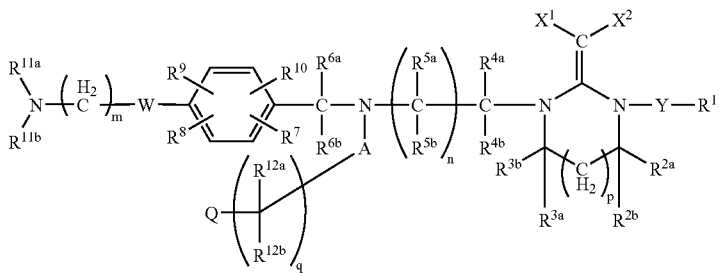

An illustrative compound of that series is:

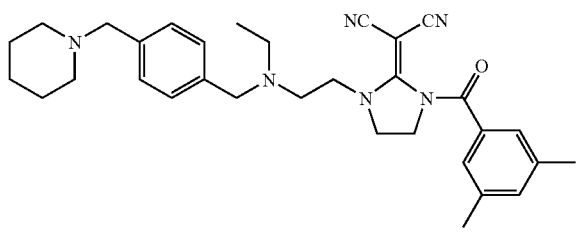

Reference is also made to PCT Publication No. WO 03/101970 (Applicant: SmithKline Beecham Corporation, Published Dec. 11, 2003) which discloses imidazolium compounds and their use as CXCR3 antagonists having the formula:

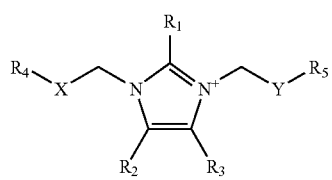

An illustrative example of that series is:

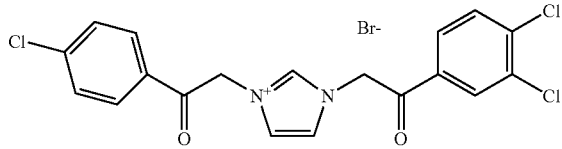

Reference is also made to US Patent Application No. US 2003/0055054 A1 (Applicant: Medina et al, Published Mar. 20, 2003) which discloses compounds having the formula:

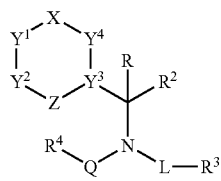

An illustrative compound of that series is:

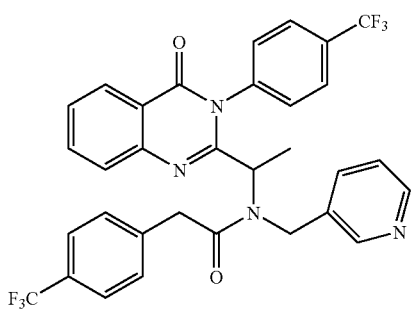

Reference is also made to U.S. Pat. No. 6,124,319 (Applicant: MacCoss et al., issued Sep. 6, 2000) which discloses compounds useful as chemokine receptor modulators having the formula:

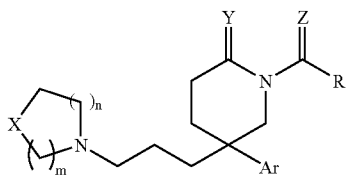

Reference is also made to PCT Publication WO 03/070242 A1 (Applicant: CELLTECH R& D limited, Published Aug. 28, 2003) which discloses compounds useful as "chemokine receptor inhibitors for the treatment of inflammatory diseases" having the formula:

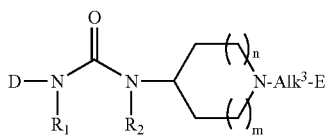

There is a need for compounds that are capable of modulating CXCR3 activity. For example, there is a need for new treatments and therapies for diseases and conditions associated with CXCR3 such as inflammatory conditions (psoriasis and inflammatory bowel disease), autoimmune disease (multiple sclerosis, rheumatoid arthritis) and graft rejection (allograft and zenograft rejections for example) as well as infectious diseases, cancers and tumors, fixed drug eruptions, cutaneous delayed-type hypersensitivity responses, type I diabetes, viral meningitis and tuberculoid leprosy.

There is a need for methods of treatment or prevention or amelioration of one or more symptoms of diseases and conditions associated with CXCR3. There is a need for methods for modulating CXCR3 activity using the compounds provided herein.

SUMMARY OF THE INVENTION

In its many embodiments, the invention provides novel compounds of the Formula 1:

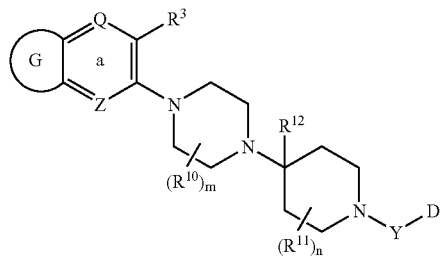

Formula 1 or a pharmaceutically acceptable salt, solvate or ester thereof, wherein:

Q is N, NO, NOH or C($R^4$);

Z is N, NO, NOH or C($R^{29}$);

G represents a 5 to 7 membered heteroaryl, heterocyclenyl or heterocyclyl ring containing at least one N atom as ring atom of said heteroaryl, heterocyclenyl or heterocyclyl ring, wherein each of said heteroaryl, heterocyclenyl or heterocyclyl ring optionally additionally contains on the ring one or more moieties which moieties can be the same or different, each being independently selected from the group consisting of N,N(→O), O, S, S(O) and S($O_2$), further wherein each of said heteroaryl, heterocyclenyl or heterocyclyl ring is either (i) unsubstituted, or (ii) optionally independently substituted on one or more ring carbon atoms with one or more $R^9$ substituents, and independently on one or more ring nitrogen atoms with one or more $R^8$ substituents, wherein said one or more $R^9$ substituents can be the same or different, and said one or more $R^8$ substituents can be the same or different, further wherein said G ring is fused to ring marked a in Formula 1 via carbon atom, heteroatom or both;

$R^3$, $R^4$, and $R^{29}$ can be the same or different, each being independently selected from the group consisting of H, alkyl, alkylaryl, aralkyl, —CN, $CF_3$, haloalkyl, cycloalkyl, halogen, hydroxyalkyl, —N=CH—($R^{31}$), —C(=O)N($R^{30})_2$, —N($R^{30})_2$, —$OR^{30}$, —$SO_2(R^{31})$, —N($R^{30}$)C(=O)N($R^{30})_2$ and —N($R^{30}$)C(=O)$R^{31}$;

the $R^8$ moieties can be the same or different, each being independently selected from the group consisting of H, alkyl, alkenyl, alkylaryl, arylalkyl, cycloalkyl, aryl, heteroaryl, heterocyclyl, —($CH_2)_qOH$, —($CH_2)_qOR^{31}$, —($CH_2)_qNH_2$, —($CH_2)_qNHR^{31}$, —($CH_2)_qC(=O)NHR^{31}$, —($CH_2)_qC(=O)OR^{31}$, —($CH_2)_qSO_2R^{31}$, —($CH_2)_qNSO_2R^{31}$, and —($CH_2)_qSO_2NHR^{31}$;

the $R^9$ moieties can be the same or different, each being independently selected from the group consisting of H, alkyl, alkenyl, alkylaryl, arylalkyl, alkoxy, amidinyl, aryl, cycloalkyl, cyano, heteroaryl, heterocyclyl, hydroxyl, —C(=O)N($R^{30})_2$, —C(=S)N($R^{30})_2$, —C(=O)alkyl, —($CH_2)_qOH$, —($CH_2)_qOR^{31}$, ($CH_2)_qNH_2$, —($CH_2)_q NHR^{31}$, —($CH_2)_qC(=O)NHR^{31}$, —($CH_2)_qSO_2R^{31}$, —($CH_2)_qNSO_2R^{31}$, —($CH_2)_qSO_2NHR^{31}$, —N($R^{30})_2$, —N($R^{30}$)S($O_2$)$R^{31}$, —N($R^{30}$) C(=O)N($R^{30})_2$, —$OR^{30}$, —$SO_2(R^{31})$, —$SO_2N(R^{30})_2$, =O and =S;

the $R^{10}$ moieties can be the same or different, each being independently selected from the group consisting of H, alkyl, cycloalkyl, aryl, heteroaryl, heterocyclenyl, heterocyclyl, alkylaryl, arylalkyl, —$CO_2H$, hydroxyalkyl, —C(=O)N ($R^{30})_2$, —($CH_2)_qOH$, —($CH_2)_qOR^{31}$—$OR^{30}$, halogen, =O, and —C(=O)$R^{31}$;

the $R^{11}$ moieties can be the same or different, each being independently selected from the group consisting of H, alkyl, cycloalkyl, aryl, heteroaryl, heterocyclyl, heterocyclenyl, alkylaryl, arylalkyl, carboxamide, $CO_2H$, —($CH_2)_qOH$, —($CH_2)_qOR^{31}$, —$OR^{30}$, halogen, =O, and —C(=O)$R^{31}$;

$R^{12}$ moieties can be the same or different, each being independently selected from the group consisting of H, alkyl, —CN, —C(=O)N($R^{30})_2$, —($CH_2)_qOH$, —($CH_2)_qOR^{31}$ and —S($O_2$)$R^{31}$;

ring D is a five to nine membered cycloalkyl, cycloalkenyl, aryl, heteroaryl, heterocyclenyl or heterocyclyl ring having 0-4 heteroatoms independently selected from O, S or N, wherein ring D is unsubstituted or optionally substituted with 1-5 independently selected $R^{20}$ moieties;

the $R^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —($CH_2)_qOH$, ($CH_2)_qOR^{31}$, —($CH_2)_qNH_2$, —($CH_2)_qNHR^{31}$, —($CH_2)_qC(=O)NHR^{31}$, —($CH_2)_qSO_2R^{31}$, —($CH_2)_qNSO_2R^{31}$, —($CH_2)_qSO_2NHR^{31}$, -alkynylC($R^{31})_2$ $OR^{31}$, —C(=O)$R^{30}$, —C(=O)N($R^{30})_2$, —C(=N$R^{30}$) $NHR^{30}$, —C(=NOH)N($R^{30})_2$, —C(=NO$R^{31}$)N($R^{30})_2$, —C(=O)$OR^{30}$, —N($R^{30})_2$, —N($R^{30}$)C(=O)$R^{31}$, —NHC (=O)N($R^{30})_2$, —N($R^{30}$)C(=O)$OR^{31}$, —N($R^{30}$)C(=NCN) N($R^{30})_2$, —N($R^{30}$)C(=O)N($R^{30}$)$SO_2(R^{31}$), —N($R^{30}$)C (=O)N($R^{30})_2$, —N($R^{30}$)$SO_2(R^{31}$), —N($R^{30}$)S(O)$_2$N($R^{30})_2$, —$OR^{30}$, —OC(=O)N($R^{30})_2$, —$SR^{30}$, —$SO_2N(R^{30})_2$, —$SO_2(R^{31})$, —$OSO_2(R^{31})$, and —$OSi(R^{30})_3$; or alternatively two $R^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 $R^{21}$ moieties;

the $R^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —($CH_2)_qOH$, —($CH_2)_qOR^{31}$, —($CH_2)_q NH_2$, —($CH_2)_qNHR^{31}$, —($CH_2)_qC(=O)NHR^{31}$, —($CH_2)_q SO_2R^{31}$, —($CH_2)_qNSO_2R^{31}$, —($CH_2)_qSO_2NHR^{31}$, -alkynylC($R^{31})_2OR^{31}$, —C(=O)$R^{30}$, —C(=O)N($R^{30})_2$, —C(=N$R^{30}$)$NHR^{30}$, —C(=NOH)N($R^{30})_2$, —C(=NO$R^{31}$)N($R^{30})_2$, —C(=O)$OR^{30}$, —N($R^{30})_2$, —N($R^{30}$)C(=O)$R^{31}$, —NHC(=O)N($R^{30})_2$, —N($R^{30}$)C (=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$;

Y is selected from the group consisting of —(CR$^{13}$R$^{13}$)$_r$—, —CHR$^{13}$C(=O)—, —(CHR$^{13}$)$_r$O—, —(CHR$^{13}$)$_r$N(R$^{30}$)—, —C(=O)—, —C(=NR$^{30}$)—, —C(=N—OR$^{30}$)—, —CH(C(=O)NHR$^{30}$)—, CH-heteroaryl-, —C(R$^{13}$R$^{13}$)$_r$C(R$^{13}$)=C(R$^{13}$)—, —(CHR$^{13}$)$_r$C(=O)— and —(CHR$^{13}$)$_r$N(H)C(=O)—; or alternatively Y is cycloalkyl, heterocyclenyl, or heterocyclyl wherein the cycloalkyl, heterocyclenyl, or heterocyclyl is fused with ring D;

the R$^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, —CN, —CO$_2$H, —C(=O)R$^{30}$, —C(=O)N(R$^{30}$)$_2$, —(CHR$^{30}$)$_q$OH, —(CHR$^{30}$)$_q$OR$^{31}$, —(CHR$^{30}$)$_q$NH$_2$, —(CH R$^{30}$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, —NH$_2$, —N(R$^{30}$)$_2$, —N(R$^{30}$)C(=O)N(R$^{30}$)$_2$, —N(R$^{30}$)SO$_2$(R$^{31}$), —OH, OR$^{30}$, —SO$_2$N(R$^{30}$)$_2$, and —SO$_2$(R$^{31}$);

the R$^{30}$ moieties can be the same or different, each being independently selected from the group consisting of H, alkyl, alkylaryl, aryl, aralkyl, cycloalkyl, —CN, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

the R$^{31}$ moieties can be the same or different, each being independently selected from the group consisting of alkyl, alkylaryl, aryl, aralkyl, cycloalkyl, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and hetroaryl;

m is 0 to 4;

n is 0 to 4;

each q can be the same or different, each being independently selected from 1 to 5; and r is 1 to 4;

with the proviso that there are no two adjacent double bonds in any ring, and that when a nitrogen is substituted by two alkyl groups, said two alkyl groups may be optionally joined to each other to form a ring.

A further feature of the invention is a pharmaceutical composition containing as active ingredient at least one compound of Formula 1 together with at least one pharmaceutically acceptable carrier or excipient.

The invention provides methods of preparing compounds of Formula 1, as well as methods for treating diseases, for example, treatment (e.g., palliative therapy, curative therapy, prophylactic therapy) of certain diseases and conditions e.g., inflammatory diseases (e.g., psoriasis, inflammatory bowel disease), autoimmune diseases (e.g., rheumatoid arthritis, multiple sclerosis), graft rejection (e.g., allograft rejection, xenograft rejection), ophthalmic inflammation or dry eye, infectious diseases and tumors. The invention provides a method of treating a CXCR3 chemokine mediated disease in a patient in need of such treatment comprising administering to the patient a therapeutically effective amount of at least one compound of Formula 1, or a pharmaceutically acceptable salt, solvate or ester thereof.

The invention provides methods of treating diseases, for example, treatment (e.g., palliative therapy, curative therapy, prophylactic therapy) of certain diseases and conditions such as inflammatory diseases (e.g., psoriasis, inflammatory bowel disease), autoimmune diseases (e.g., rheumatoid arthritis, multiple sclerosis), graft rejection (e.g., allograft rejection, xenograft rejection), infectious diseases as well as cancers and tumors, fixed drug eruptions, cutaneous delayed-type hypersensitivity responses, ophthalmic inflammation or dry eye, type I diabetes, viral meningitis and tuberculoid leprosy comprising administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (such as cyclosporins and methotrexate); steroids (including corticosteroids such as glucorticoids); PDE IV inhibitors, anti-TNF-α compounds, TNF-α-convertase (TACE) inhibitors, MMP inhibitors, cytokine inhibitors, glucocorticoids, other chemokine inhibitors such as CCR2 and CCR5, CB2-selective inhibitors, p38 inhibitors, biological response modifiers; anti-inflammatory agents and therapeutics.

The invention also provides a method of modulating (inhibiting or promoting) an inflammatory response in an individual in need of such therapy. The method comprises administering a therapeutically effective amount of a compound (e.g., small organic molecule) which inhibits or promotes mammalian CXCR3 function in an individual in need thereof. Also disclosed is a method of inhibiting or blocking T-cell mediated chemotaxis in a patient in need of such treatment comprising administering to the patient a therapeutically effective amount of a compound of Formula 1 or a pharmaceutically acceptable salt, solvate or ester thereof.

Also disclosed is a method of treating inflammatory bowel disease (such Crohn's disease, ulcerative colitis) in a patient in need of such treatment comprising administering to the patient a therapeutically effective amount of at least one compound of Formula 1, or a pharmaceutically acceptable salt, solvate or ester thereof.

Also disclosed is a method of treating inflammatory bowel disease in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: sulfasalazine, 5-aminosalicylic acid, sulfapyridine, anti-TNF compounds, anti-IL-12 compounds, corticosteroids, glucocorticoids, T-cell receptor directed therapies (such as anti-CD3 antibodies), immunosuppresives, methotrexate, azathioprine, and 6-mercaptopurines.

Also disclosed is a method of treating graft rejection in a patient in need of such treatment comprising administering to the patient a therapeutically effective amount of at least one compound of Formula 1, or a pharmaceutically acceptable salt, solvate or ester thereof.

Also disclosed is a method of treating graft rejection in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: cyclosporine A, FK-506, FTY720, beta-interferon, rapamycin, mycophenolate, prednisolone, azathioprine, cyclophosphamide and an antilymphocyte globulin.

Also disclosed is a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: beta-interferon, glatiramer acetate, corticosteroids, glucocorticoids, methotrexate, azothioprine, mitoxantrone, VLA4 inhibitors, FTY720, anti-IL-12 inhibitors, and CB2-selective inhibitors.

Also disclosed is a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: methotrexate, cyclosporin, leflunomide, sulfasalazine, corticosteroids, β-methasone, β-interferon, glatiramer acetate, prednisone, etonercept, and infliximab.

Also disclosed is a method of treating rheumatoid arthritis in a patient in need of such treatment the method comprising administering to the patient a therapeutically effective amount of: (a) at least one compound of Formula 1, or a pharmaceutically acceptable salt, solvate or ester thereof concurrently or sequentially with (b) at least one compound selected from the group consisting of: non-steroidal anti-inflammatory agents, COX-2 inhibitors, COX-1 inhibitors, immunosuppressives, cyclosporine, methotrexate, steroids, PDE IV inhibitors, anti-TNF-α compounds, MMP inhibitors, corticosteroids, glucocorticoids, chemokine inhibitors, CB2-selective inhibitors, caspase (ICE) inhibitors and other classes of compounds indicated for the treatment of rheumatoid arthritis.

Also disclosed is a method of treating psoriasis in a patient in need of such treatment the method comprising administering to the patient a therapeutically effective amount of: a) at least one compound of Formula 1, or a pharmaceutically acceptable salt, solvate or ester thereof concurrently or sequentially with (b) at least one compound selected from the group consisting of: immunosuppressives, cyclosporins, methotrexate, steroids, corticosteroids, anti-TNF-α compounds, anti-IL compounds, anti-IL-23 compounds, vitamin A and D compounds and fumarates.

Also disclosed is a method of treating ophthalmic inflammation (including, for e.g., uveitis, posterior segment intraocular inflammation, Sjogren's syndrome) or dry eye in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, FK506, steroids, corticosteroids, and anti-TNF-α compounds.

Also disclosed is a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, ophthalmic inflammation (including e.g., uveitis, posterior segment intraocular inflammation, and Sjogren's syndrome), tuberculoid leprosy and cancer in a patient in need of such treatment, such method comprising administering to the patient an effective amount of at least one compound according to Formula 1, or a pharmaceutically acceptable salt, solvate or ester thereof.

The invention also provides a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, ophthalmic inflammation, type I diabetes, viral meningitis and cancer in a patient in need of such treatment, such method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; PDE IV inhibitors, anti-TNF-α compounds, MMP inhibitors, corticosteroids, glucocorticoids, chemokine inhibitors, CB2-selective inhibitors, biological response modifiers; anti-inflammatory agents and therapeutics.

DETAILED DESCRIPTION OF THE INVENTION

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

As used above, and throughout the specification, the following terms, unless otherwise indicated, shall be understood to have the following meanings:

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The alkenyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, heterocyclenyl, amino, aminosulfonyl, halo, carboxyl, carboxyalkyl (non-limiting example(s) include ester), alkoxycarbonyl, hydroxyalkyl, carbonyl (non-limiting example(s) include ketone), —C(=O)heterocyclyl, formyl (non-limiting example(s) include aldehyde), carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl), —NHC(=O)alkyl, urea (e.g. —NH(C=O)NH$_2$, —NH(C=O)NH(alkyl), —NH(C=O)NH(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e. —CO$_2$NH$_2$), NHC(=O)Oalkyl, —CO$_2$N(alkyl)$_2$, —NHC(=O))NH—S(O)$_2$alkyl, —NHC(=O)N(alkyl)$_2$—S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, alkylthiocarboxy, —S(O)$_2$alkyl, —S(O)$_2$aryl, —OS(O)$_2$alkyl, —OS(O)$_2$aryl, sulfonyl urea (non-limiting example(s) include NHC(=S)NHalkyl). Non-limiting examples of suitable alkenyl groups include ethenyl, propenyl, n-butenyl, 3-methylbut-2-enyl, n-pentenyl, octenyl and decenyl.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, heterocyclenyl,
amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), alkoxycarbonyl, hydroxyalkyl, carbonyl (non-limiting example(s) include ketone), —C(=O)heterocyclyl, formyl, carboxamido (i.e. amido, —C(=O)NH$_2$, —C(=O)N(alkyl)$_2$, —C(=O)NH(alkyl), —C(=O)N(cycloalkyl)$_2$, —C(=O)NH(cycloalkyl)), —NHC(=O)alkyl, amidinyl, hydrazidyl, hydroxamate, —NHC(=O)H, —NHC(=O)alkyl, urea (non-limiting example(s) include —NH(C=O)NH$_2$, —NH(C=O)NH(alkyl), —NH(C=O)N(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e., —CO$_2$NH$_2$), —NHC(=O)Oalkyl, —CO$_2$N(alkyl)$_2$, —NHC(=O)NH—S(O)$_2$alkyl, —NHC(=O)N(alkyl)-S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, thio, alkylthio, alkylthiocarboxy, —S(O)alkyl, —S(O)$_2$alkyl, —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkylheteroaryl" means an alkyl-heteroaryl-group wherein the alkyl is as previously described and the bond to the parent moiety is through the heteroaryl group.

"Alkylamino" means an —NH2 or —NH3+ group in which one or more of the hydrogen atoms on the nitrogen is replaced by an alkyl group as defined above. The bond to the parent is through the nitrogen.

"Alkylaryl" means an alkyl-aryl-group in which the alkyl and aryl are as described herein. Preferred alkylaryls comprise a lower alkyl group. Non-limiting examples of suitable alkylaryl groups include o-tolyl, p-tolyl and xylyl. The bond to the parent moiety is through the aryl.

"Alkylthio" means an alkyl-S— group in which the alkyl group is as described herein. Non-limiting examples of suitable alkylthio groups include methylthio, ethylthio, i-propylthio and heptylthio. The bond to the parent moiety is through the sulfur.

"Alkylthiocarboxy" means an alkyl-S—C(=O)O— group. Preferred groups are those in which the alkyl group is lower alkyl. The bond to the parent moiety is through the carboxy.

"Alkylsulfonyl" means an alkyl-S(O)$_2$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, alkoxyl, aryl, aryloxy, cycloalkyl, cycloalkenyl, cyano, heteroaryl, heterocyclyl, heterocyclenyl, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, alkoxycarbonyl, hydroxyalkyl, carbonyl (non-limiting example(s) include ketone), —C(=O)heterocyclyl, carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl)), alkylC(=O)NH—, —NHC(=O)alkyl, urea (e.g. —NH(C=O)NH$_2$), —NH(C=O)NH(alkyl), —NH(C=O)NH(alkyl)$_2$, —NH(C=O)NH(heteroaryl), —NH(C=O)NH(heterocyclyl), —S(O)$_2$alkyl, and —S(O)$_2$aryl.

"Alkoxy" means an alkyl-O— group in which the alkyl group is as previously described. Non-limiting examples of suitable alkoxy groups include methoxy, ethoxy, n-propoxy, isopropoxy, n-butoxy, heptoxy and methylhydroxy. The bond to the parent moiety is through the ether oxygen.

"Alkoxycarbonyl" means an alkyl-O—C(=O)— group. Non-limiting examples of suitable alkoxycarbonyl groups include methoxycarbonyl and ethoxycarbonyl. The bond to the parent moiety is through the carbonyl.

"Aminoalkyl" means an amine-alkyl-group in which alkyl is as previously defined. Preferred aminoalkyls contain lower alkyl. Non-limiting examples of suitable aminoalkyl groups include aminomethyl and 2-Dimethlylamino-2-ethyl. The bond to the parent moiety is through the alkyl.

"Amidinyl" means —C(=NR)NHR group. The R groups are defined as H, alkyl, alkylaryl, heteroaryl, hydroxyl, alkoxy, amino, ester, CN, —NHSO₂alkyl, —NHSO₂Aryl, —NHC(=O)NHalkyl, and —NHalkyl. The bond to the parent moiety is through the carbon.

"Aralkyl" or "arylalkyl" means an aryl-alkyl-group in which the aryl and alkyl are as previously described. Preferred aralkyls comprise a lower alkyl group attached to the aryl group. Non-limiting examples of suitable aralkyl groups include phenymethylene, 2-phenethyl and naphthalenylmethyl. The bond to the parent moiety is through the alkyl.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkylthio" means an aralkyl-S— group in which the aralkyl group is as previously described. Non-limiting example of a suitable aralkylthio group is benzylthio. The bond to the parent moiety is through the sulfur.

"Aralkoxy" means an aralkyl-O— group in which the aralkyl group is as described above. The bond to the parent moiety is through the oxygen group.

"Aralkoxycarbonyl" means an aralkyl-O—C(=O)— group. Non-limiting example of a suitable aralkoxycarbonyl group is benzyloxycarbonyl. The bond to the parent moiety is through the carbonyl.

"Aroyl" means an aryl-C(=O)— group in which the aryl group is as previously described. The bond to the parent moiety is through the carbonyl. Non-limiting examples of suitable groups include benzoyl and 1- and 2-naphthoyl.

"Aryl" (sometimes abbreviated "Ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxycarbonyl" means an aryl-O—C(=O)— group. Non-limiting examples of suitable aryloxycarbonyl groups include phenoxycarbonyl and naphthoxycarbonyl. The bond to the parent moiety is through the carbonyl.

"Arylsulfonyl" means an aryl-S(O)₂— group. The bond to the parent moiety is through the sulfonyl.

"Arylsulfinyl" means an aryl-S(O)— group. The bond to the parent moiety is through the sulfinyl.

"Arylthio" means an aryl-S— group in which the aryl group is as previously described. Non-limiting examples of suitable arylthio groups include phenylthio and naphthylthio. The bond to the parent moiety is through the sulfur.

"Carboxyalkyl" means an alkyl-C(=O)O— group. The bond to the parent moiety is through the carboxy.

"Carboxamido" means —C(=O)NRR wherein R is H, alkyl, amino, aryl, cycloalkyl, heterocyclenyl, heteroaryl and carboxamido. The bond to the parent moiety is through the carboxy.

Carbamates and urea substituents refer to groups with oxygens and nitrogens respectively adjacent an amide; representative carbamate and urea substituents include the following:

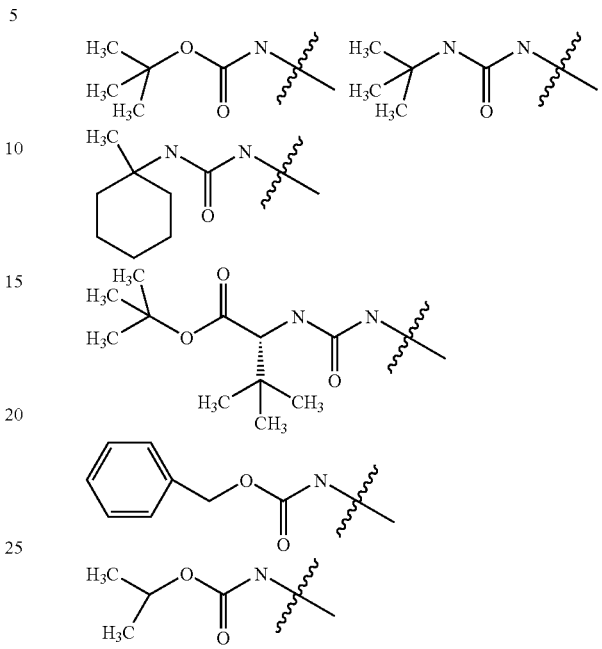

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples can include bicyclic cycloalkyls such as bicycloheptane. Non-limiting examples of suitable multicyclic cycloalkyls include 1-decalin, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl. The term "cycloalkenyl" additionally means moieties such as cyclobutenedione, cyclopentenone, cyclopentenedione and the like.

"Halogen" (or halo) means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination.

Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. The nitrogen or sulfur atom of the heteroaryl can be optionally oxidized to the corresponding N-oxide, S-oxide or S,S-dioxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, oxazolidinyl, imidazolidinyl, thiomorpholinyl, thiazolidinyl, 1,3-dioxolanyl, 1,4-d ioxanyl, tetrahydrofuranyl, tetrahydrothiophenyl, tetrahydrothiopyranyl, and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetra hydropyrimidine, dihydro-2-pyrrolinyl, dihydro-3-pyrrolinyl, dihydro-2-imidazolinyl, dihydro-2-pyrazolinyl, dihydro-4,5-trizolyl and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include thiophenyl, dihydrothiophenyl, dihydrothiopyranyl, and the like.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-(3-yl)methyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl. The bond to the parent moiety is through the alkyl.

"Hydroxamate" means an alkyl-C(=O)NH—O— group. The bond to the parent moiety is through the oxygen group.

"Spiroalkyl" means an alkylene group wherein two carbon atoms of an alkyl group are attached to one carbon atom of a parent molecular group thereby forming a carbocyclic or heterocyclic ring of three to eleven atoms. Representative structures include examples such as:

The spiroalkyl groups of this invention:

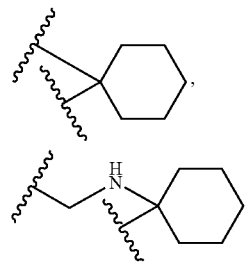

can be optionally substituted by one or more ring system substituents, wherein "ring system substituent" is as defined herein.

"Ring system substituent" means a substituent attached to an aromatic or non-aromatic ring system which, for example, replaces an available hydrogen on the ring system. Ring system substituents may be the same or different, each being independently selected from the group consisting of H, alkyl, alkenyl, alkynyl, alkoxyl, aryl, aroyl, aryloxy, cycloalkyl, cycloalkenyl, heteroaryl, heterocyclyl, heterocyclenyl, alkylaryl, alkylheteroaryl, aralkyl, aralkenyl, aralkoxy, aralkoxycarbonyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), cyano, alkoxycarbonyl, hydroxyalkyl, carbonyl (non-limiting example(s) include ketone), —C(=O)heterocyclyl, formyl (non-limiting example(s) include aldehyde), carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl), alkylC(=O)NH—, -amidino, hydrazido, hydroxamate, —NHC(=O)H, —NHC(=O)alkyl, urea (e.g. —NH(C=O)NH$_2$), —NH(C=O)NH(alkyl), —NH(C=O)N(alkyl)$_2$, —NH(C=O)NH(heteroaryl), —NH(C=O)NH(heterocyclyl), guanidinyl, —NHC(=NCN)NH$_2$, —NHC(=NCN)N (alkyl)₂, carbamoyl (i.e. —CO₂NH₂), NHC(=O)Oalkyl, —CO₂N(alkyl)₂, —NHC(=O))NH—S(O)₂alkyl, —NHC(=O)N(alkyl)₂—S(O)₂alkyl, —NH—S(O)₂alkyl, —NH—S(O)₂heteroaryl, —N(alkyl)-S(O)₂alkyl, —NH—S(O)₂aryl, —N(alkyl)-S(O)₂aryl, —NH—S(O)₂NH₂, —NH—S(O)₂NHalkyl, —NH—S(O)₂N(alkyl)₂, thio, alkylthiocarboxy, —S(O)₂alkyl —S(O)₂aryl, —OS(O)₂alkyl, —OS(O)₂aryl, sulfonyl urea (non-limiting example(s) include —NHC(=S)NHalkyl) and OSi(alkyl)₃.

"Ring system substituent" also means a cyclic ring of 3 to 7 ring atoms of which may contain 1 or 2 heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

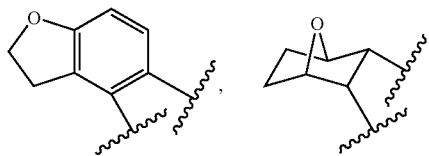

and the like.

The term "optionally substituted" means optional substitution with the specified groups, radicals or moieties, in available position or positions.

With reference to the number of moieties (non-limiting example(s) include, substituents, groups or rings) in a compound, unless otherwise defined, the phrases "one or more" and "at least one" mean that, there can be as many moieties as chemically permitted, and the determination of the maximum number of such moieties is well within the knowledge of those skilled in the art. Preferably, there are one to three substituents, or more preferably, one to two substituents, with at least one in the para position.

As used herein, the term "composition" is intended to encompass a product comprising the specified ingredients in the specified amounts, as well as any product which results, directly or indirectly, from combination of the specified ingredients in the specified amounts.

The straight line —— as a bond generally indicates a mixture of, or either of, the possible isomers, non-limiting example(s) include, containing (R)- and (S)-stereochemistry. For example,

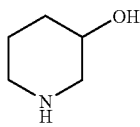

means containing both

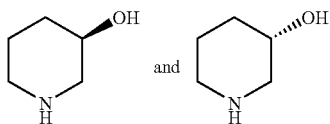

Lines drawn into the ring systems, such as, for example:

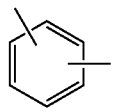

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

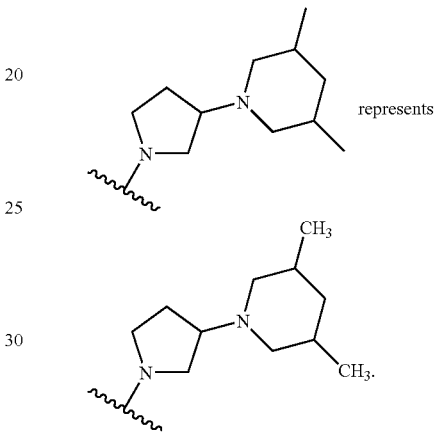

It should also be noted that any heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

Metabolic conjugates, for example, glucoronides and sulfates which can under reversible conversion to compounds of Formula 1 are contemplated in this application.

"Effective amount" or "therapeutically effective amount" is meant to describe an amount of compound or a composition of the present invention effective to antagonize CXCR3 and thus produce the desired therapeutic effect in a suitable patient.

"Mammal" means humans and other mammalian animals.

"Patient" includes both human and animals.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula 1 form salts which are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (non-limiting example(s) include, non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in The Orange Book (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (non-limiting example(s) include methyl, ethyl, propyl, and butyl chlorides, bromides and iodides), dialkyl sulfates (non-limiting example(s) include dimethyl, diethyl, dibutyl, and diamyl sulfates), long chain halides (non-limiting example(s) include decyl, lauryl, myristyl and stearyl chlorides, bromides and iodides), aralkyl halides (non-limiting example(s) include benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula 1, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

It should also be noted that throughout the specification and Claims appended hereto any formula, compound, moiety or chemical illustration with unsatisfied valences is assumed to have the hydrogen atom to satisfy the valences unless the context indicates a bond.

In one embodiment, the present invention discloses compounds of Formula 1, having CXCR3 antagonist activity, or a pharmaceutically acceptable derivative thereof, where the various definitions are given above.

In another embodiment, G is fused to said ring marked a via at least said one N atom of ring G.

In another embodiment, ring G is selected from the group consisting of:

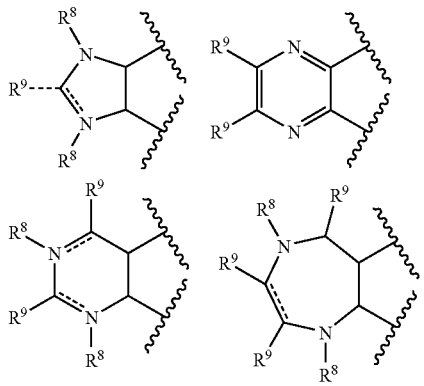

wherein ----- is a single bond or double bond.

In another embodiment, $R^3$ is selected from the group consisting of H, alkyl, haloalkyl, hydroxyalkyl, halogen, —N($R^{30}$)$_2$, —O$R^{30}$ and —CF$_3$.

In another embodiment, $R^3$ is selected from the group consisting of H, —CH$_3$, —CH$_2$CH$_3$, cyclopropyl, —F, —Cl, OCH$_3$, OCF$_3$ and CF$_3$.

In another embodiment, $R^4$ is selected from the group consisting of H, alkyl, halogen, hydroxyalkyl, —CN, —N($R^{30}$)$_2$, —O$R^{30}$, —N=CH-alkyl, and —N$R^{30}$C(=O)alkyl.

In another embodiment, $R^4$ is selected from the group consisting of H, —NH$_2$, —CH$_3$, —CN and —F.

In another embodiment, $R^8$ is selected from the group consisting of H, alkyl, alkenyl, arylalkyl, cycloalkyl, —(CH$_2$)$_q$OH, —(CH$_2$)$_q$O$R^{31}$, —(CH$_2$)$_q$NH$_2$, —(CH$_2$)$_q$NH$R^{31}$, —(CH$_2$)$_q$C(=O)NH$R^{31}$, —(CH$_2$)$_q$SO$_2R^{31}$, —(CH$_2$)$_q$NSO$_2R^{31}$, and —(CH$_2$)$_q$SO$_2$NH$R^{31}$.

In another embodiment, the $R^9$ moieties can be the same or different, each being independently selected from the group consisting of H, alkyl, cycloalkyl, —C(=O)N(H)$R^{30}$, —C(=O)alkyl, —(CH$_2$)$_q$OH, —(CH$_2$)$_q$O$R^{31}$, —(CH$_2$)$_q$NH$_2$, —(CH$_2$)$_q$NH$R^{31}$, —N(H)$R^{30}$, —N(H)S(O$_2$)$R^{31}$, —N(H)C(=O)NH($R^{30}$), —O$R^{30}$—SO$_2$($R^{31}$), and —SO$_2$N(H)$R^{30}$.

In another embodiment, the $R^9$ moieties can be the same or different, each being independently selected from the group consisting of H, cyclopropyl, —CF$_3$, —CH$_3$, —CH$_2$OH, —CH$_2$CH$_2$OH, —C(CH$_3$)$_2$OH, —CH$_2$CH$_2$OCH$_3$, —C(=O)OCH$_2$CH$_3$, —CH$_2$NH$_2$, —CH$_2$CH$_2$NH$_2$, —CH$_2$CH$_2$NHSO$_2$CH$_3$, —CH$_2$CH$_2$SO$_2$CH$_3$, —C(=O)NH$_2$, —C(=O)N(H)CH$_2$CH$_2$OH, —CH$_2$N(H)C(=O)CF$_3$, —C(=O)N(H)-cyclopropyl, —C(=O)N(H)CH$_2$CF$_3$, —NH$_2$, —NHCH$_3$, —N(CH$_3$)$_2$, —N(H)CH$_2$CH$_3$, —N(H)CH(CH$_3$)$_2$, —N(H)CH$_2$CH$_2$CH$_3$, —N(H)CH$_2$C(=O)OCH$_3$, —N(H)CH$_2$CH$_2$OH, —N(H)CH$_2$CH$_2$NH$_2$, —N(H)CH$_2$CH$_2$NHSO$_2$CH$_3$, —N(H)CH$_2$CH$_2$SO$_2$CH$_3$, —N(H)C(=O)N(H)CH$_2$CH$_3$, —N(H)CH$_2$C(=O)NH$_2$, —OCH$_3$, =S and =O.

In another embodiment, the $R^9$ moieties can be the same or different, each being independently selected from the group consisting of H, —CF$_3$, —CH$_3$, —CH$_2$OH, —CH$_2$CH$_2$NH$_2$, —NH$_2$, —NHCH$_3$, —N(H)CH$_2$CH$_3$, —N(H)CH(CH$_3$)$_2$, —N(H)CH$_2$CH$_2$CH$_3$, —N(H)CH$_2$C(=O)OCH$_3$, and —N(H)CH$_2$CH$_2$OH.

In another embodiment, $R^{10}$ is selected from the group consisting of H, alkyl, aralkyl, hydroxyalkyl, and carbonyl.

In another embodiment, $R^{10}$ is selected from the group consisting of —CH$_3$, —CH$_2$CH$_3$ and —CH$_2$CH$_2$CH$_3$, and m is 0-2.

In another embodiment, $R^{11}$ is selected from the group consisting of H, alkyl, hydroxyalkyl and carbonyl.

In another embodiment, $R^{11}$ is H or —CH$_3$.

In another embodiment, $R^{12}$ is selected from the group consisting of H, CN, —C(=O)N($R^{30}$)$_2$ and alkyl.

In another embodiment, $R^{12}$ is selected from the group consisting of H, —CH$_3$, CN and —CH$_2$CH$_3$.

In another embodiment, the ring atoms of ring D are independently C or N and substituted by 0-4 $R^{20}$ moieties.

In another embodiment, ring D is a 5 to 6 membered aryl, heteroaryl, heterocyclenyl, or heterocyclyl ring and substituted by 0-4 $R^{20}$ moieties.

In another embodiment, the $R^{20}$ moieties can be the same or different, each being independently selected from the group consisting of H, alkyl, alkylaryl, alkynyl, alkoxy, alkylamino, alkylheteroaryl, alkylsulfinyl, alkoxycarbonyl, aminoalkyl, amidinyl, aralkyl, aralkoxy, aryl, aryloxy, cyano, cycloalkyl, cycloalkenyl, halogen, haloalkyl, heteroalkyl, heteroaryl, heterocyclyl, hydroxyalkyl, trifluromethyl, trifluoromethoxy, —(CH$_2$)$_q$O$R^{31}$, —(CH$_2$)$_q$NH$R^{31}$, —(CH$_2$)$_q$C(=O)NH$R^{31}$, —(CH$_2$)$_q$SO$_2R^{31}$, —(CH$_2$)$_q$NSO$_2R^{31}$, —(CH$_2$)$_q$SO$_2$NH$R^{31}$, -alkynylC($R^{31}$)$_2$O$R^{31}$, —C(=O)$R^{30}$, —C(=O)N($R^{30}$)$_2$, —C(=O)O$R^{30}$, —N($R^{30}$)$_2$, —N($R^{30}$)C(=O)$R^{31}$, —NHC(=O)N($R^{30}$)$_2$, —N($R^{30}$)C(=O)O$R^{31}$, —N($R^{30}$)C(=NCN)N($R^{30}$)$_2$, —N($R^{30}$)C(=O)N($R^{30}$)$_2$, —N($R^{30}$)SO$_2$($R^{31}$), —N($R^{30}$)SO$_2$N($R^{30}$)$_2$, —O$R^{30}$, —OC(=O)N($R^{30}$)$_2$, —S$R^{30}$, —SO$_2$N($R^{30}$)$_2$, —SO$_2$($R^{31}$), —OSO$_2$($R^{31}$), and —OSi($R^{30}$)$_3$.

In another embodiment, the $R^{20}$ moieties can be the same or different, each being independently selected from the group consisting of H, alkyl, amino, halogen, CN, CH$_3$, CF$_3$, OCF$_3$, —(CH$_2$)$_q$O$R^3$, —(CH$_2$)$_q$NH$R^{31}$, —(CH$_2$)$_q$C(=O)NH$R^{31}$, —(CH$_2$)$_q$SO$_2R^{31}$, —(CH$_2$)$_q$NSO$_2R^{31}$, —(CH$_2$)$_q$SO$_2$NH$R^{31}$, -alkynylC($R^{31}$)$_2$O$R^{31}$, —C(=O)$R^{30}$, —C(=O)O$R^{30}$, —N($R^{30}$)$_2$, —N($R^{30}$)C(=O)$R^{31}$, —NHC(=O)N($R^{30}$)$_2$, —N($R^{30}$)C(=O)O$R^{31}$, —N($R^{30}$)C(=NCN)N($R^{30}$)$_2$, —N($R^{30}$)C(=O)N($R^{30}$)$_2$, —O$R^{30}$, —OC(=O)N($R^{30}$)$_2$, and —OSO$_2$($R^{31}$).

In another embodiment, two $R^{20}$ moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 $R^{21}$ moieties.

In another embodiment, the $R^{20}$ moieties can be the same or different, each being independently selected from the group consisting of H, —CN, —CH$_3$, —CF$_3$, —CH$_2$OH, —CO$_2$H, —CO$_2$CH$_3$, —NH$_2$, —NHCH$_3$, —OCF$_3$, —OH, F, Cl, Br, —C(=NOH)NH$_2$, —OCH$_2$CH$_2$S(O$_2$)CH$_3$, —C(=O)NH$_2$,

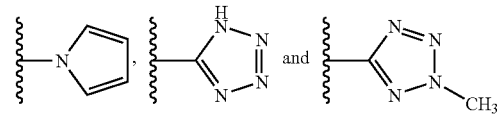

In another embodiment, Y is selected from the group consisting of: —(CH$R^{13}$)$_r$—, —(C$R^{13}R^{13}$)$_r$—, —C(=O)— and —CH$R^{13}$C(=O)—.

In another embodiment, Y is selected from the group consisting of: —CH$_2$—, —CH(CH$_3$)—, —CH(CH$_2$OH)—, —C(=O)— and —CH(CO$_2$alkyl)-.

In another embodiment, m is 0-2.

In another embodiment, n is 0-2.

In another embodiment, q is 1 or 2.

In another embodiment, r is 1 or 2.

In another embodiment, ring G is selected from the group consisting of:

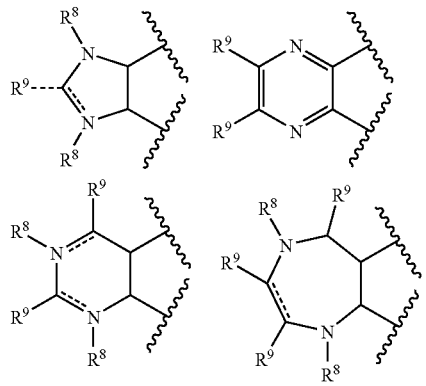

----- is a single bond or a double bond;

$R^3$ is selected from the group consisting of H, alkyl, haloalkyl, hydroxyalkyl, halogen, —N(R$^{30}$)$_2$, —OR$^{30}$ and —CF$_3$;

$R^6$ is selected from the group consisting of H, alkyl, halogen, hydroxyalkyl, —CN, —N(R$^{30}$)$_2$, —OR$^{30}$, —N=CH-alkyl, and —NR$^{30}$OC(=O)alkyl;

$R^9$ moieties can be the same or different, each being independently selected from the group consisting of H, alkyl, cycloalkyl, —C(=O)N(H)R$^{30}$, —C(=O)alkyl, —(CH$_2$)$_q$OH, —(CH$_2$)$_q$OR$^{31}$, —(CH$_2$)$_q$NH$_2$, —(CH$_2$)$_q$NHR$^{31}$, —N(H)R$^{30}$, —N(H)S(O$_2$)R$^{31}$, —N(H)C(=O)NH(R$^{30}$), —OR$^{30}$, —SO$_2$(R$^{31}$), and —SO$_2$N(H)R$^{30}$;

$R^{10}$ is selected from the group consisting of H, alkyl, aralkyl, hydroxyalkyl, and carbonyl;

$R^{11}$ is selected from the group consisting of: H, alkyl, hydroxyalkyl, and carbonyl;

$R^{12}$ is selected from the group consisting of H, CN, —C(=O)N(R$^{30}$)$_2$ and alkyl;

ring D is a 5 to 6 membered aryl, heteroaryl, heterocyclenyl, or heterocyclyl ring and substituted by 0-4 R$^{20}$ moieties;

the R$^{20}$ moieties can be the same or different, each being independently selected from the group consisting of H, alkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —OR$^{30}$, —OC(=O)N(R$^{30}$)$_2$,

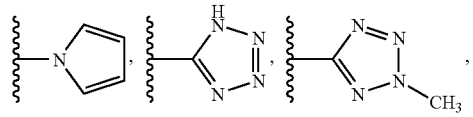

and —OSO$_2$(R$^{31}$)

Y is selected from the group consisting of: —CH$_2$—, —CH(CH$_3$)—, —CH(CH$_2$OH)—, —C(=O)— and —CH(CO$_2$alkyl)-;

m is 0-2;

n is 0-2;

q is 1 or 2; and r is 1 or 2.

In another embodiment, the compound of Formula 1 is represented by structural Formula 2, Formula 3, Formula 4 or Formula 5:

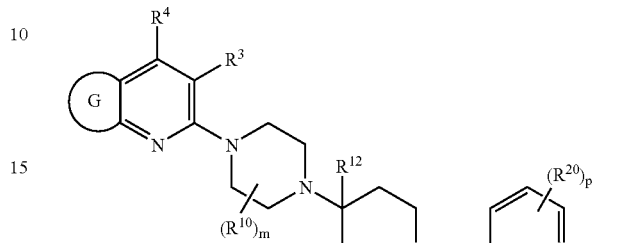

Formula 2

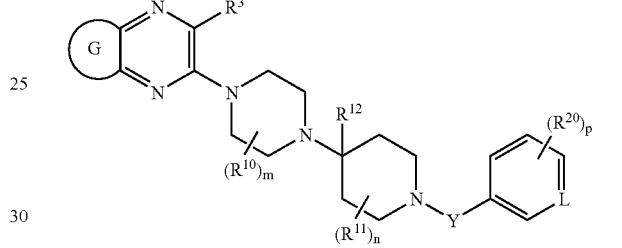

Formula 3

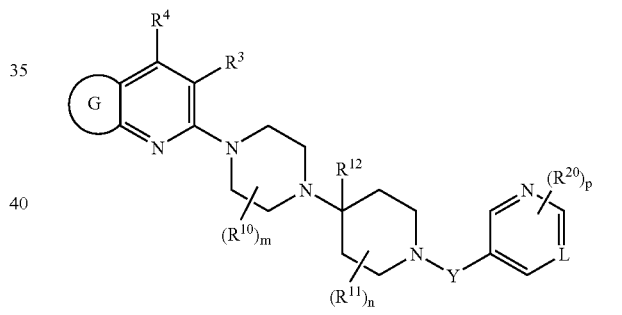

Formula 4

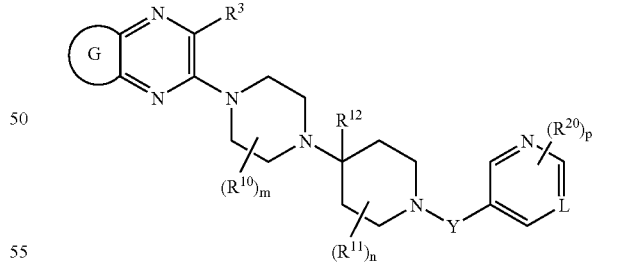

Formula 5 wherein:

the R$^8$ moieties can be the same or different, each being independently selected from the group consisting of H, alkyl, alkenyl, alkylaryl, arylalkyl, cycloalkyl, aryl, heteroaryl, heterocyclenyl, heterocyclyl, —(CH$_2$)$_q$OH, (CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, or —(CH$_2$)$_q$SO$_2$NHR$^{31}$;

the R$^9$ moieties can be the same or different, each being independently selected from the group consisting of H, alkyl, arylalkyl, alkylaryl, cycloalkyl, heteroaryl, heterocyclenyl, heterocyclyl, —C(=O)N(H)R$^{30}$, —C(=O)alkyl, —N(H)R$^{30}$, —N(H)S(O$_2$)R$^{31}$, —N(H)C(=O)NH(R$^{30}$), —OR$^{30}$, —SO$_2$(R$^{31}$), =O, =S, and —SO$_2$N(H)R$^{30}$;

L is C or N; and m, n, q, R$^{10}$, R$^{11}$, R$^{12}$, R$^{20}$ and Y are as defined in claim 1.

In another embodiment, in the above-shown Formula 2, Formula 3, Formula 4 or Formula 5, R$^3$ is selected from the group consisting of H, alkyl, haloalkyl, hydroxyalkyl, halogen, —N(R$^{30}$)$_2$, —OR$^{30}$ and —CF$_3$.

In another embodiment, in the above-shown Formula 2, Formula 3, Formula 4 or Formula 5, R$^6$ is selected from the group consisting of H, alkyl, halogen, —N(R$^{30}$)$_2$, —OR$^{30}$ and —NR$^1$C(=O)alkyl.

In another embodiment, in the above-shown Formula 2, Formula 3, Formula 4 or Formula 5, R$^9$ moieties are the same or different, each being independently selected from the group consisting of H, cyclopropyl, —CF$_3$, —CH$_3$, —CH$_2$CH$_3$, —CH$_2$OH, —CH$_2$CH$_2$OH, —C(CH$_3$)$_2$OH, —CH$_2$CH$_2$OCH$_3$, —C(=O)OCH$_2$CH$_3$, —CH$_2$NH$_2$, —CH$_2$CH$_2$NH$_2$, —CH$_2$CH$_2$NHSO$_2$CH$_3$, —CH$_2$CH$_2$SO$_2$CH$_3$, —C(=O)NH$_2$, —C(=O)N(H)CH$_2$CH$_2$OH, —CH$_2$N(H)C(=O)CF$_3$, —C(=O)N(H)-cyclopropyl, —C(=O)N(H)CH$_2$CF$_3$, —NH$_2$, —NHCH$_3$, —N(CH$_3$)$_2$, —N(H)CH$_2$CH$_3$, —N(H)CH(CH$_3$)$_2$, —N(H)CH$_2$CH$_2$CH$_3$, —N(H)CH$_2$C(=O)OCH$_3$, —N(H)CH$_2$CH$_2$OH, —N(H)CH$_2$CH$_2$NH$_2$, —N(H)CH$_2$CH$_2$NHSO$_2$CH$_3$, —N(H)CH$_2$CH$_2$SO$_2$CH$_3$, —N(H)C(=O)N(H)CH$_2$CH$_3$, —N(H)CH$_2$C(=O)NH$_2$, =O, =S, and —OCH$_3$.

In another embodiment, in the above-shown Formula 2, Formula 3, Formula 4 or Formula 5, R$^{10}$ is selected from the group consisting of H, alkyl, aralkyl, hydroxyalkyl, and carbonyl.

In another embodiment, in the above-shown Formula 2, Formula 3, Formula 4 or Formula 5, R$^{11}$ is selected from the group consisting of: H, alkyl and carbonyl.

In another embodiment, in the above-shown Formula 2, Formula 3, Formula 4 or Formula 5, R$^{12}$ is selected from the group consisting of H, —CH$_3$, CN or —CH$_2$CH$_3$.

In another embodiment, in the above-shown Formula 2, Formula 3, Formula 4 or Formula 5, R$^{20}$ moieties can be the same or different, each being independently selected from the group consisting of H, alkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —OR$^{30}$, —OC(=O)N(R$^{30}$)$_2$, —OSO$_2$(R$^{31}$),

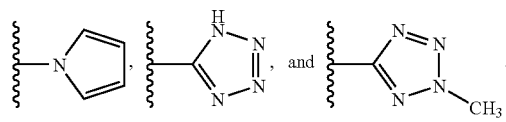

In another embodiment, in the above-shown Formula 2, Formula 3, Formula 4 or Formula 5, the R$^{20}$ moieties can be the same or different, each being independently selected from the group consisting of H, —CN, —CH$_3$, —CF$_3$, —CH$_2$OH, —CO$_2$H, —CO$_2$CH$_3$, —NH$_2$, —NHCH$_3$, —OCF$_3$, —OH, F, Cl, Br, —C(=NOH)NH$_2$, —OCH$_2$CH$_2$S(O$_2$)CH$_3$, —C(=O)NH$_2$,

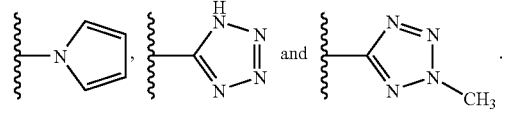

In another embodiment, in the above-shown Formula 2, Formula 3, Formula 4 or Formula 5, L is carbon.

In another embodiment, in the above-shown Formula 2, Formula 3, Formula 4 or Formula 5, L is nitrogen.

In another embodiment, in the above-shown Formula 2, Formula 3, Formula 4 or Formula 5, Y is selected from the group consisting of: —CH$_2$—, —C(=O)—, —CH(CH$_2$OH)— and —CH(CO$_2$alkyl)-.

In another embodiment, in the above-shown Formula 2, Formula 3, Formula 4 or Formula 5, R$^3$ is selected from the group consisting of H, alkyl, haloalkyl, hydroxyalkyl, halogen, —N(R$^{30}$)$_2$, —OR$^{30}$ and —CF$_3$;

R$^6$ is selected from the group consisting of H, alkyl, halogen, —N(R$^{30}$)$_2$, —OR$^{30}$, and —NR$^1$C(=O)alkyl;

the R$^9$ moieties can be the same or different, each being independently selected from the group consisting of H, alkyl, cycloalkyl, —C(=O)N(H)R$^{30}$, —C(=O)alkyl, —N(H)R$^{30}$, —N(H)S(O$_2$)R$^{31}$, —N(H)C(=O)NH(R$^{30}$), —OR$^{30}$, —SO$_2$(R$^{31}$), and —SO$_2$N(H)R$^{30}$;

R$^{10}$ is selected from the group consisting of H, alkyl, aralkyl, hydroxyalkyl and carbonyl;

the R$^{20}$ moieties can be the same or different, each being independently selected from the group consisting of H, alkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —OR$^{30}$, —OC(=O)N(R$^{30}$)$_2$, and —OSO$_2$(R$^{31}$),

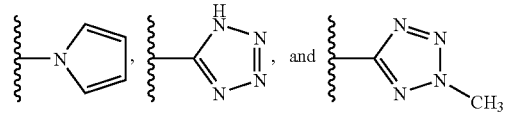

Y is selected from the group consisting of: —CH$_2$—, —C(=O)—, —CH(CH$_2$OH)— and —CH(CO$_2$alkyl)-;

m is 0-2;

q is 1, 2 or 3; and r is 1 or 2.

In still another embodiment of the present invention, a compound is selected from the following structures in Table 1 below (or a pharmaceutically acceptable salt or solvate thereof) which are shown along with their IC$_{50}$ ratings. The IC$_{50}$ values are rated, "A" for IC$_{50}$ values less than about 25 nanomolar (nM), "B" for IC$_{50}$ values in the range of from about 25 to about 100 nM and "C" for IC$_{50}$ values greater than about 100 nM. For example, Compound Number 1 has a IC$_{50}$ value of 0.3 nM.

TABLE 1

| Compound Number | STRUCTURE | IC$_{50}$ |
|---|---|---|
| 1 | 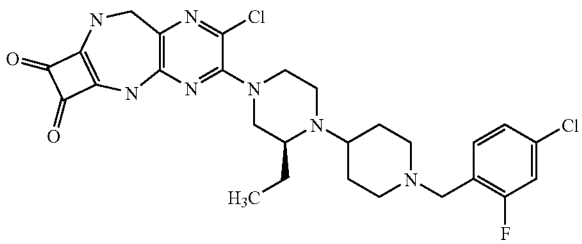 | A |
| 2 | 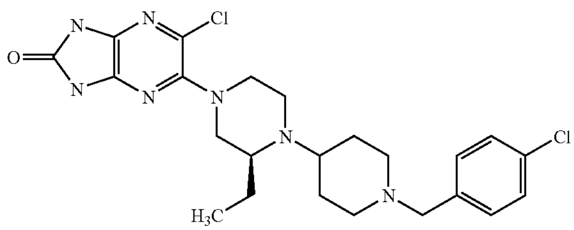 | A |
| 3 | 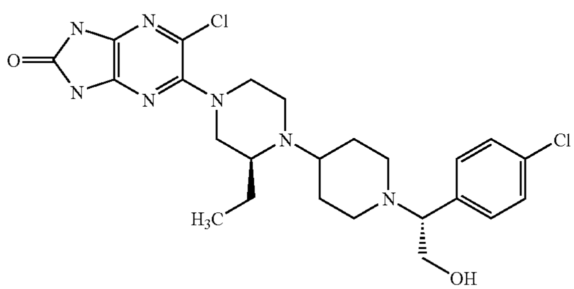 | A |
| 4 | 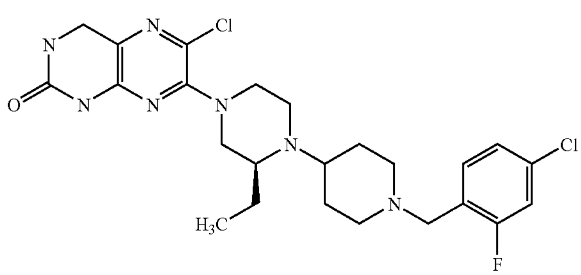 | A |
| 5 | 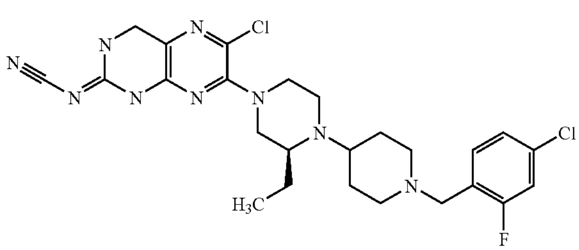 | A |
| 6 | 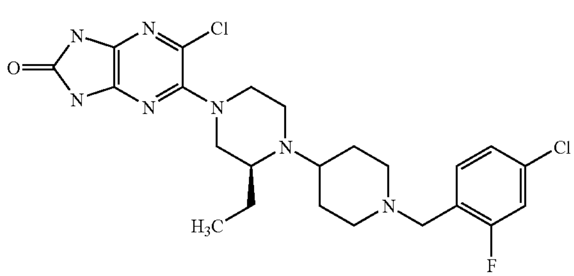 | A |

TABLE 1-continued
| Compound Number | STRUCTURE | IC$_{50}$ |
|---|---|---|
| 7 | 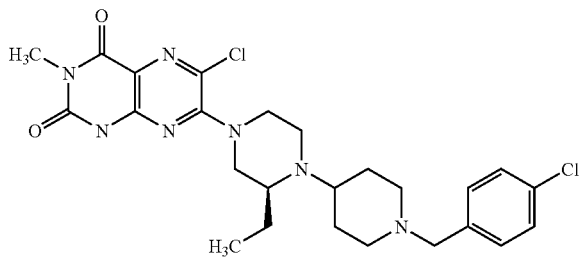 | A |
| 8 | 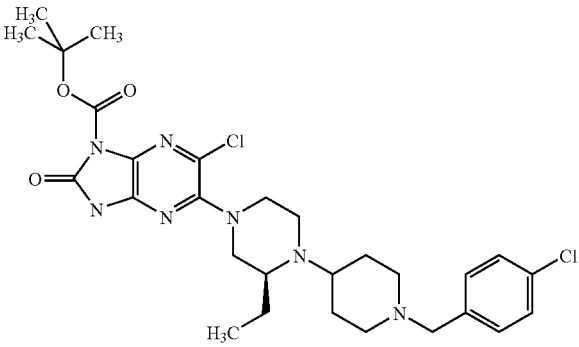 | A |
| 9 | 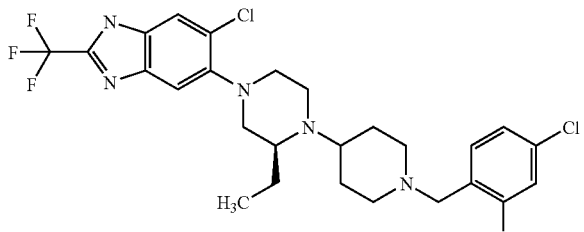 | A |
| 10 | 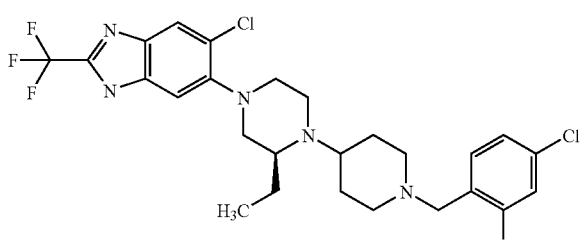 | A |
| 11 | 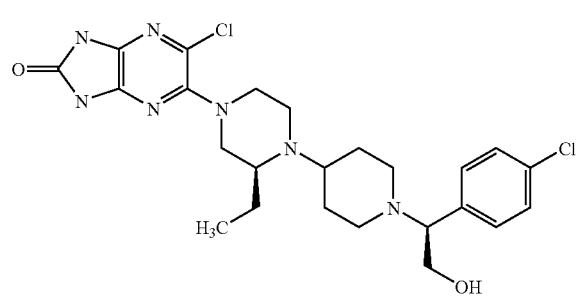 | A |

TABLE 1-continued

| Compound Number | STRUCTURE | IC$_{50}$ |
|---|---|---|
| 12 | 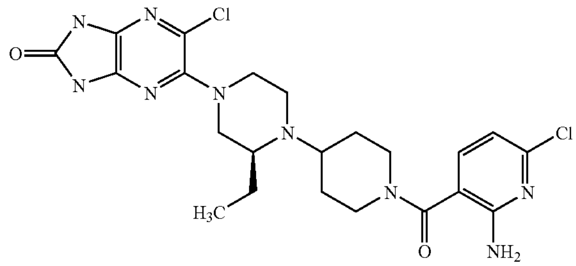 | A |
| 13 | 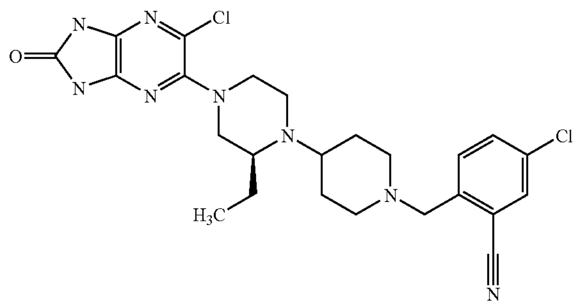 | A |
| 14 | 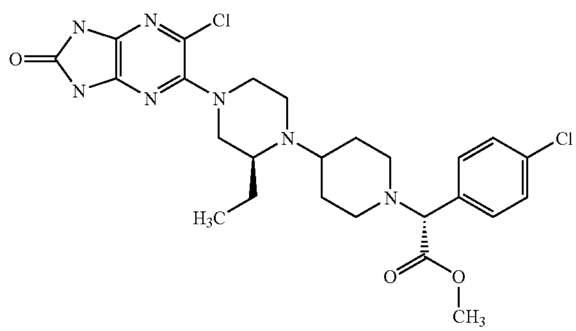 | A |
| 15 | 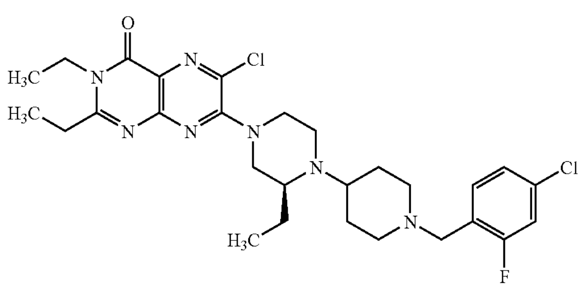 | A |
| 16 | 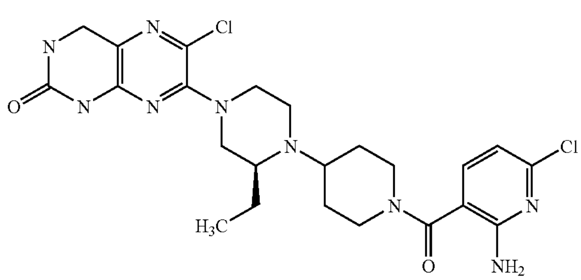 | A |

TABLE 1-continued

| Compound Number | STRUCTURE | IC$_{50}$ |
|---|---|---|
| 17 | 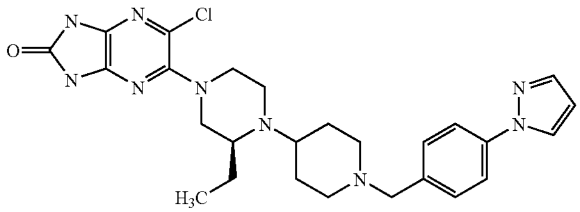 | A |
| 18 | 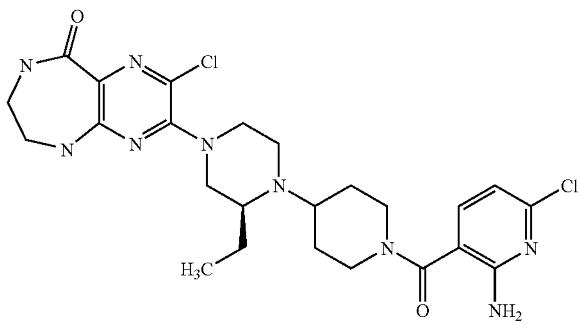 | B |
| 19 | 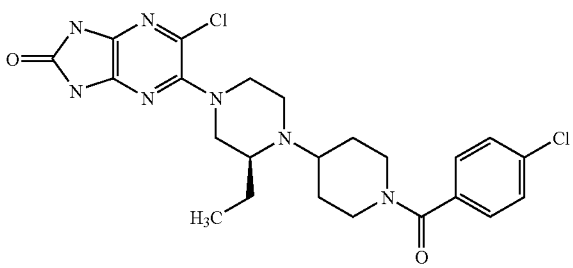 | B |
| 20 | 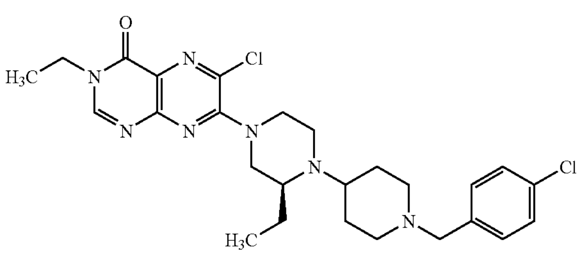 | B |
| 21 | 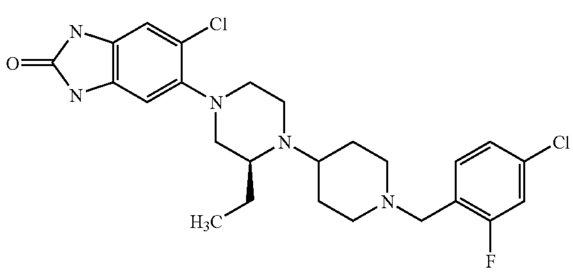 | B |

TABLE 1-continued

| Compound Number | STRUCTURE | IC$_{50}$ |
|---|---|---|
| 22 | 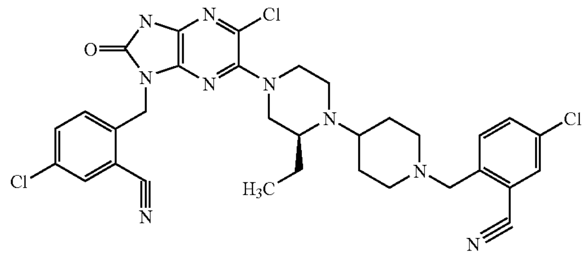 | B |
| 23 | 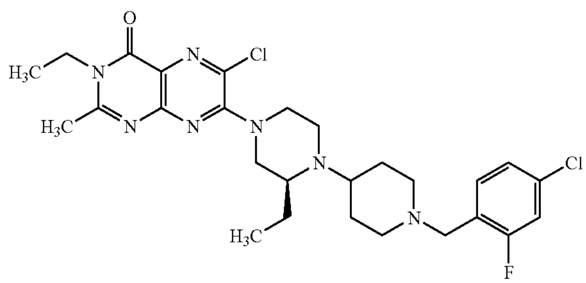 | B |
| 24 | 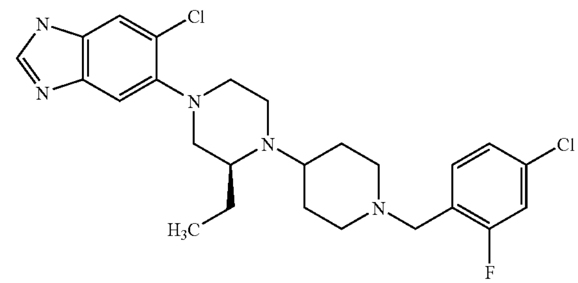 | B |
| 25 | 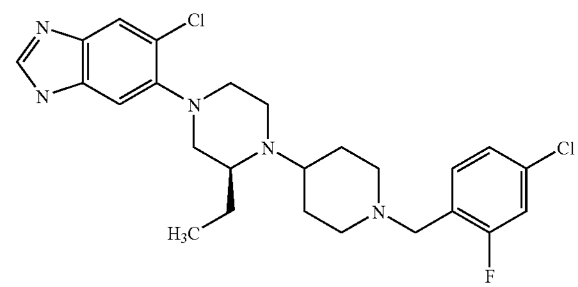 | C |
| 26 | 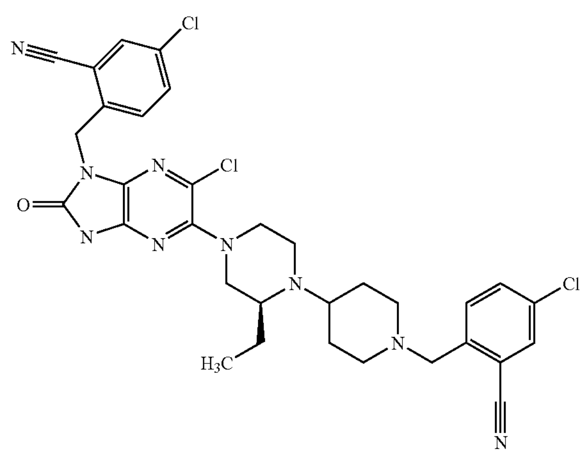 | C |

TABLE 1-continued

| Compound Number | STRUCTURE | IC$_{50}$ |
|---|---|---|
| 27 | 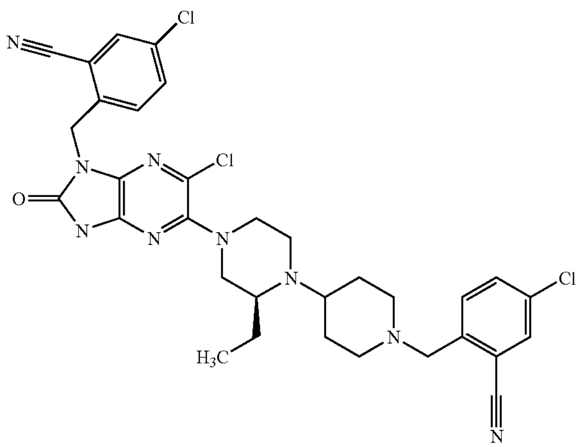 | C |
| 28 | 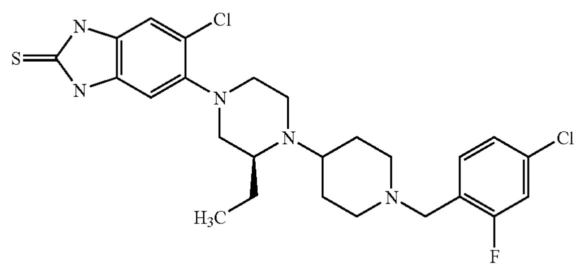 | C |
| 29 | 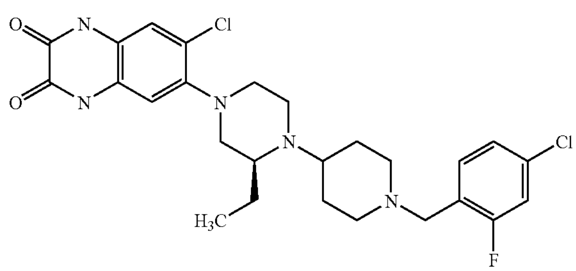 | C |
| 30 | 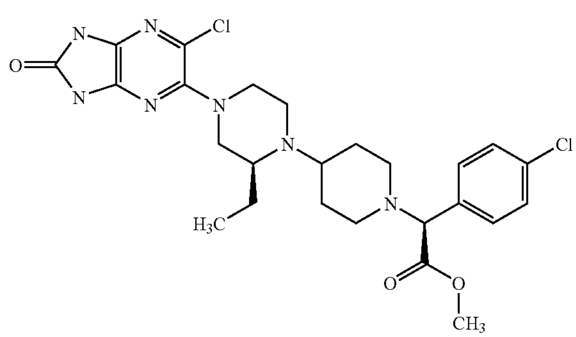 | C |

TABLE 1-continued

| Compound Number | STRUCTURE | IC$_{50}$ |
|---|---|---|
| 31 | 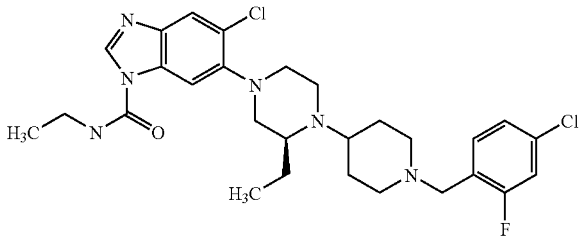 | C |
| 32 | 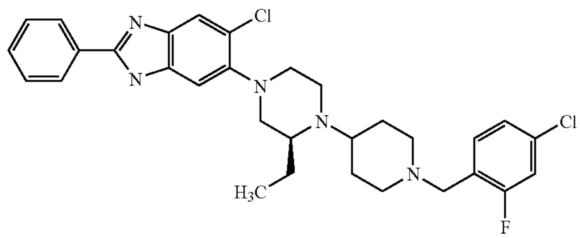 | C |
| 33 | 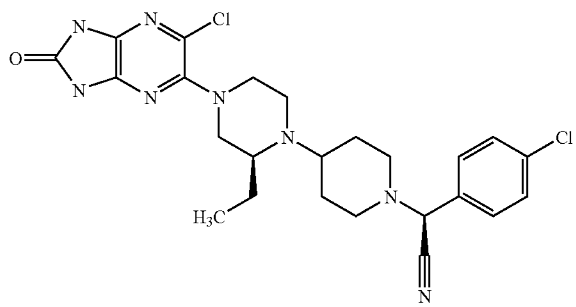 | C |
| 34 | 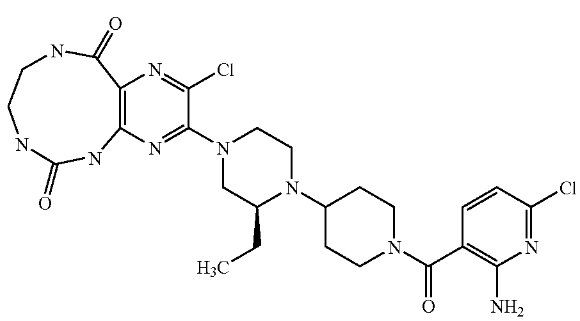 | C |
| 35 | 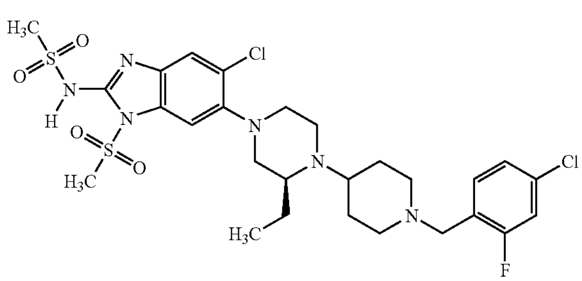 | C |

TABLE 1-continued
| Compound Number | STRUCTURE | IC$_{50}$ |
| --- | --- | --- |
| 36 | 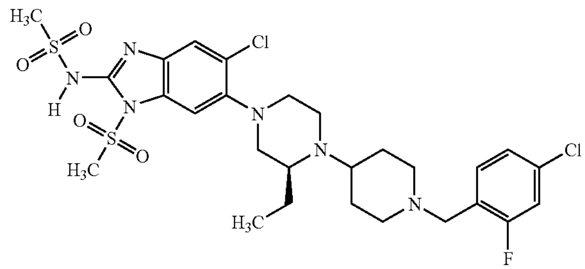 | C |
| 37 | 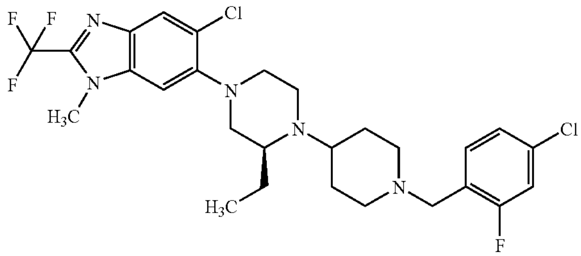 | C |
| 38 | 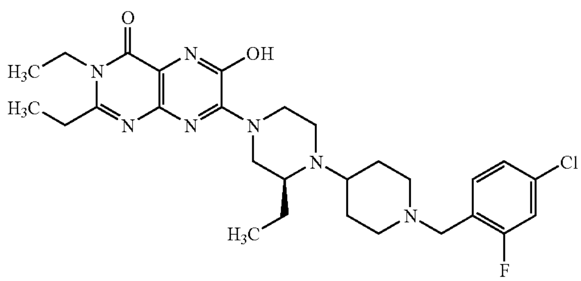 | C |
or a pharmaceutically acceptable salt, solvate or ester thereof.
For example, the compound according to Formula 1 can be selected from the group consisting of compounds of the formulae:
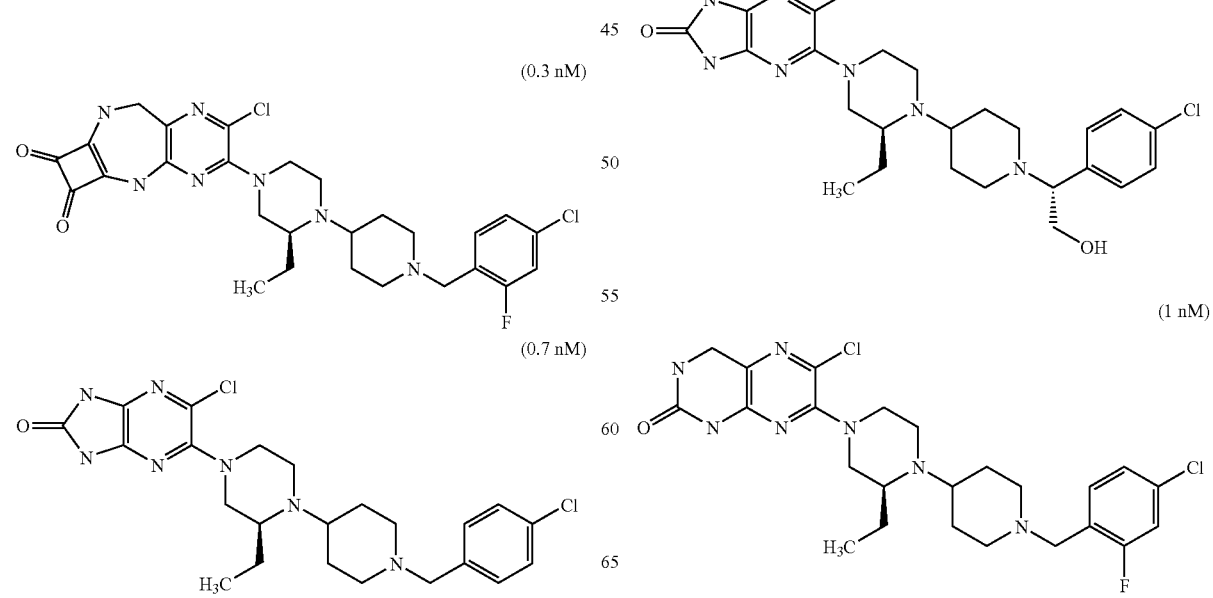

-continued

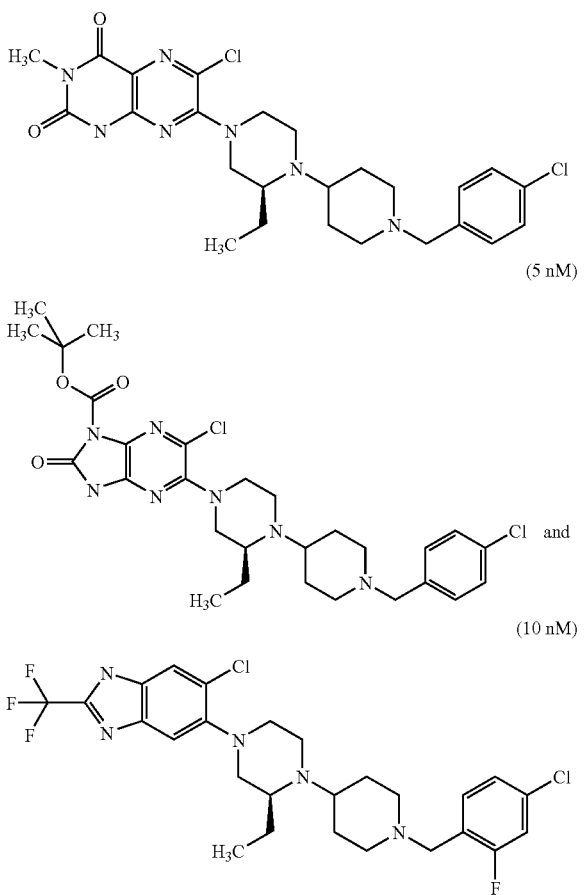

(5 nM)

(5 nM)

(10 nM)

or a pharmaceutically acceptable salt, solvate or ester thereof. The human $IC_{50}$ values (in nM) of the above compounds have been set forth above underneath their chemical structures.

In yet another aspect, this invention discloses the following compounds:

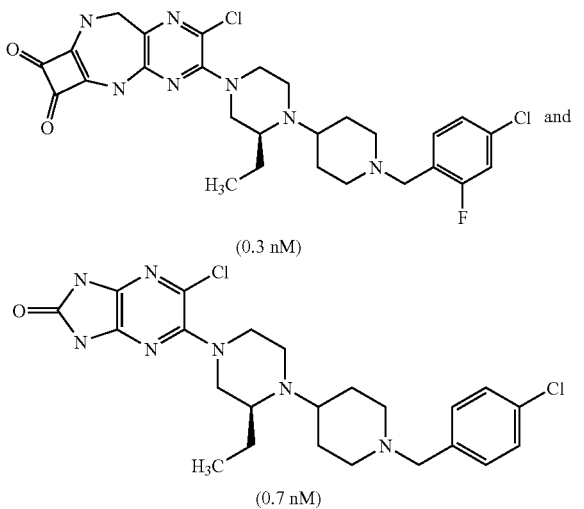

(0.3 nM)

(0.7 nM)

or pharmaceutically acceptable salts, solvates or esters thereof. The human $IC_{50}$ values (in nM) of the above compounds have been set forth above underneath their chemical structures.

In yet another aspect, the compound according to Formula 1 is in purified form.

In another embodiment, this invention provides a pharmaceutical composition comprising at least one compound of Formula 1, or a pharmaceutically acceptable salt, solvate or ester thereof in combination with at least one pharmaceutically acceptable carrier.

In still another embodiment, the invention provides a pharmaceutical composition of Formula 1, further comprising at least one additional agent, drug, medicament, antibody and/or inhibitor for treating a CXCR3 chemokine receptor mediated disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of Formula III and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In yet another embodiment, the present invention discloses methods for preparing pharmaceutical compositions comprising the inventive heterocyclic substituted piperazine compounds of Formula 1 as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents.

The tablet can be prepared by compression of mixtures or granulations obtained by wet granulation, dry granulation or by compaction.

Oral gels—efers to the active ingredients dispersed or solubilized in a hydrophillic semi-solid matrix.

Powders for constitution—refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disinteqrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellu lose and sodium carboxymethylcellu lose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

It will be apparent to those skilled in the art that many modifications, variations and alterations to the present disclosure, both to materials and methods, may be practiced. Such modifications, variations and alterations are intended to be within the spirit and scope of the present invention.

As stated earlier, the invention includes tautomers, enantiomers and other stereoisomers of the compounds also. Thus, as one skilled in the art knows, certain imidazole compounds may exist in tautomeric forms. Such variations are contemplated to be within the scope of the invention. Certain compounds of the present invention may exist in multiple crystalline forms or amorphous forms. All physical forms of the current invention are contemplated.

Compounds of this invention which contain unnatural proportions of atomic isotopes (i.e. "radiolabeled compounds") whether their use is therapeutic, diagnostic or as a research reagent are contemplated under this invention.

Another embodiment of the invention discloses the use of the pharmaceutical compositions disclosed above for treatment of diseases of a CXCR3 chemokine receptor mediated disease in a patient in need of such treatment comprising administering to the patient a therapeutically effective amount of at least one compound according to Formula 1, or a pharmaceutically acceptable salt, solvate or ester thereof.

In another embodiment, the method is directed to administering to the patient (a) an effective amount of at least one compound according to Formula 1, or a pharmaceutically acceptable salt, solvate or ester thereof concurrently or sequentially with (b) at least one additional agent, drug, medicament, antibody and/or inhibitor for treating a CXCR3 chemokine receptor mediated disease, in combination with a pharmaceutically acceptable carrier.

In another embodiment, at least one compound of Formula 1 binds to a CXCR3 receptor.

The method can further comprise administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (such as cyclosporins and methotrexate); steroids (including corticosteroids such as glucocorticoids); PDE IV inhibitors, anti-TNF-α compounds, TNF-α-convertase (TACE) inhibitors, MMP inhibitors, cytokine inhibitors, glucocorticoids, other chemokine inhibitors such as CCR2 and CCR5, CB2-selective inhibitors, p38 inhibitors, biological response modifiers; anti-inflammatory agents and therapeutics. The disease can be an inflammatory disease (e.g., psoriasis, inflammatory bowel disease)

Another embodiment of this invention is directed to a method of inhibiting or blocking T-cell mediated chemotaxis in a patient in need of such treatment the method comprising administering to the patient a therapeutically effective amount of at least one compound according to Formula 1 or a pharmaceutically acceptable salt, solvate or ester thereof.

Another embodiment of this invention is directed to a method of treating inflammatory bowel disease (such Crohn's disease, ulcerative colitis) in a patient in need of such treatment comprising administering to the patient a therapeutically effective amount of at least one compound according to Formula 1, or a pharmaceutically acceptable salt, solvate or ester thereof.

Another embodiment of this invention is directed to a method of treating inflammatory bowel disease in a patient in need of such treatment comprising administering to the patient a therapeutically effective amount of:
(a) at least one compound of Formula 1, or a pharmaceutically acceptable salt, solvate or ester thereof concurrently or sequentially with (b) at least one compound selected from the group consisting of: sulfasalazine, 5-aminosalicylic acid, sulfapyridine, anti-TNF compounds, anti-IL-12 compounds, corticosteroids, glucocorticoids, T-cell receptor directed therapies (such as anti-CD3 antibodies), immunosuppresives, methotrexate, azathioprine, and 6-mercaptopurines.

Another embodiment of this invention is directed to a method of treating or preventing graft rejection in a patient in need of such treatment comprising administering to the patient a therapeutically effective amount of at least one compound according to Formula 1, or a pharmaceutically acceptable salt, solvate or ester thereof.

Another embodiment of this invention is directed to a method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: cyclosporine A, FK-506, FTY720, beta-interferon, rapamycin, mycophenolate, prednisolone, azathioprine, cyclophosphamide and an antilymphocyte globulin.

Another embodiment of this invention is directed to a method of treating multiple sclerosis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: beta-interferon, glatiramer acetate, corticosteroids, glucocorticoids, methotrexate, azothioprine, mitoxantrone, VLA-4 inhibitors, FTY720, anti-IL-12 inhibitors, and CB2-selective inhibitors.

Another embodiment of this invention is directed to a method of treating multiple sclerosis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: methotrexate, cyclosporin, leflunomide, sulfasalazine, corticosteroids, β-methasone, β-interferon, glatiramer acetate, prednisone, etonercept, and infliximab.

Another embodiment of this invention is directed to a method of treating rheumatoid arthritis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: non-steroidal anti-inflammatory agents, COX-2 inhibitors, COX-1 inhibitors, immunosuppressives, cyclosporine, methotrexate, steroids, PDE IV inhibitors, anti-TNF-α compounds, MMP inhibitors, corticosteroids, glucocorticoids, chemokine inhibitors, CB2-selective inhibitors, caspase (ICE) inhibitors and other classes of compounds indicated for the treatment of rheumatoid arthritis.

Another embodiment of this invention is directed to a method of treating psoriasis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, steroids, corticosteroids, anti-TNF-α compounds, anti-IL compounds, anti-IL-23 compounds, vitamin A and D compounds and fumarates.

Another embodiment of this invention is directed to a method of treating ophthalmic inflammation (including, for e.g., uveitis, posterior segment intraocular inflammation, Sjogren's syndrome) or dry eye in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, FK506, steroids, corticosteroids, and anti-TNF-α compounds.

Another embodiment of this invention is directed to a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, ophthalmic inflammation (including e.g., uveitis, posterior segment intraocular inflammation, and Sjogren's syndrome), tuberculoid leprosy and cancer in a patient in need of such treatment, such method comprising administering to the patient an effective amount of at least one compound according to Formula 1, or a pharmaceutically acceptable salt, solvate or ester thereof.

Another embodiment of this invention is directed to a method of treating a disease selected from the group consisting of inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, ophthalmic inflammation, type I diabetes, viral meningitis and cancer in a patient in need of such treatment, such method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; PDE IV inhibitors, anti-TNF-α compounds, MMP inhibitors, corticosteroids, glucocorticoids, chemokine inhibitors, CB2-selective inhibitors, biological response modifiers; anti-inflammatory agents and therapeutics.

Another embodiment of the invention discloses a method of making the inventive compounds disclosed above.

Unless otherwise stated, the following abbreviations have the stated meanings in the Examples below:

DBU=1,8-diazabicyclo[5.4.0]undec-7-ene
DBN=1,5-diazabicyclo[4.3.0]non-5-ene
EDCl=1-(3-dimethylaminopropyl)-3-ethylcarbodiimide
HOBT=1-hydroxybenzotriazole
HATU=O-(7-Azabenzotriazol-1-yl)-N,N, N',N'-tetramethyluronium hexafluorophosphate
DCC=dicyclohexylcarbodiimide
Dibal-H=diisobutylaluminum hydride
LAH=lithium aluminum hydride
$NaBH(OAc)_3$=sodium triacetoxyborohydride
$NaBH_4$=sodium borohydride
$NaBH_3CN$=sodium cyanoborohydride
LDA=lithium diisopropylamide
p-TsOH=p-toluenesulfonic acid
m-CPBA=m-Chloroperbenzoic acid
TMAD=N,N,N',N'-tetramethylazod icarboxamide
CSA=camphorsulfonic acid
NaHMDS=sodium hexamethyl disilylazide
HRMS=High Resolution Mass Spectrometry
HPLC=High Performance Liquid Chromatography
LRMS=Low Resolution Mass Spectrometry
nM=nanomolar
Ki=Dissociation Constant for substrate/receptor complex
pA2=–log $EC_{50}$, as defined by J. Hey, *Eur. J. Pharmacol.*, (1995), Vol. 294, 329-335.
Ci/mmol=Curie/mmol (a measure of specific activity)
Tr=Triphenylmethyl
Tris=Tris (hydroxymethyl)aminomethane General Synthesis Compounds of the present invention can be prepared by a number of ways evident to one skilled in the art. Preferred methods include, but are not limited to, the general synthetic procedures described herein. One skilled in the art will recognize that one route will be optimal depending on the choice of appendage substituents. Additionally, one skilled in the art will recognize that in some cases the order of steps has to be controlled to avoid functional group incompatibilities. One skilled in the art will recognize that a more convergent route (i.e. non-linear or preassembly of certain portions of the molecule) is a more efficient method of assembly of the target compounds. Methods for the preparation of compounds of general Formula 1 where variables [$R^1$, $R^3$, $R^{10}$, $R^{11}$, $R^{12}$, $R^{20}$, T, X, Q, V, Z, Q, L Y, k, m, n, o, w and p] as defined above, are shown in schemes 1 through scheme 5. $Pr^1$, $Pr^2$ and $Pr^3$ are protecting groups exemplified below.

The prepared compounds may be analyzed for their composition and purity as well as characterized by standard analytical techniques such as, for example, elemental analysis, NMR, mass spectroscopy, and IR spectroscopy.

Scheme 1. Method A
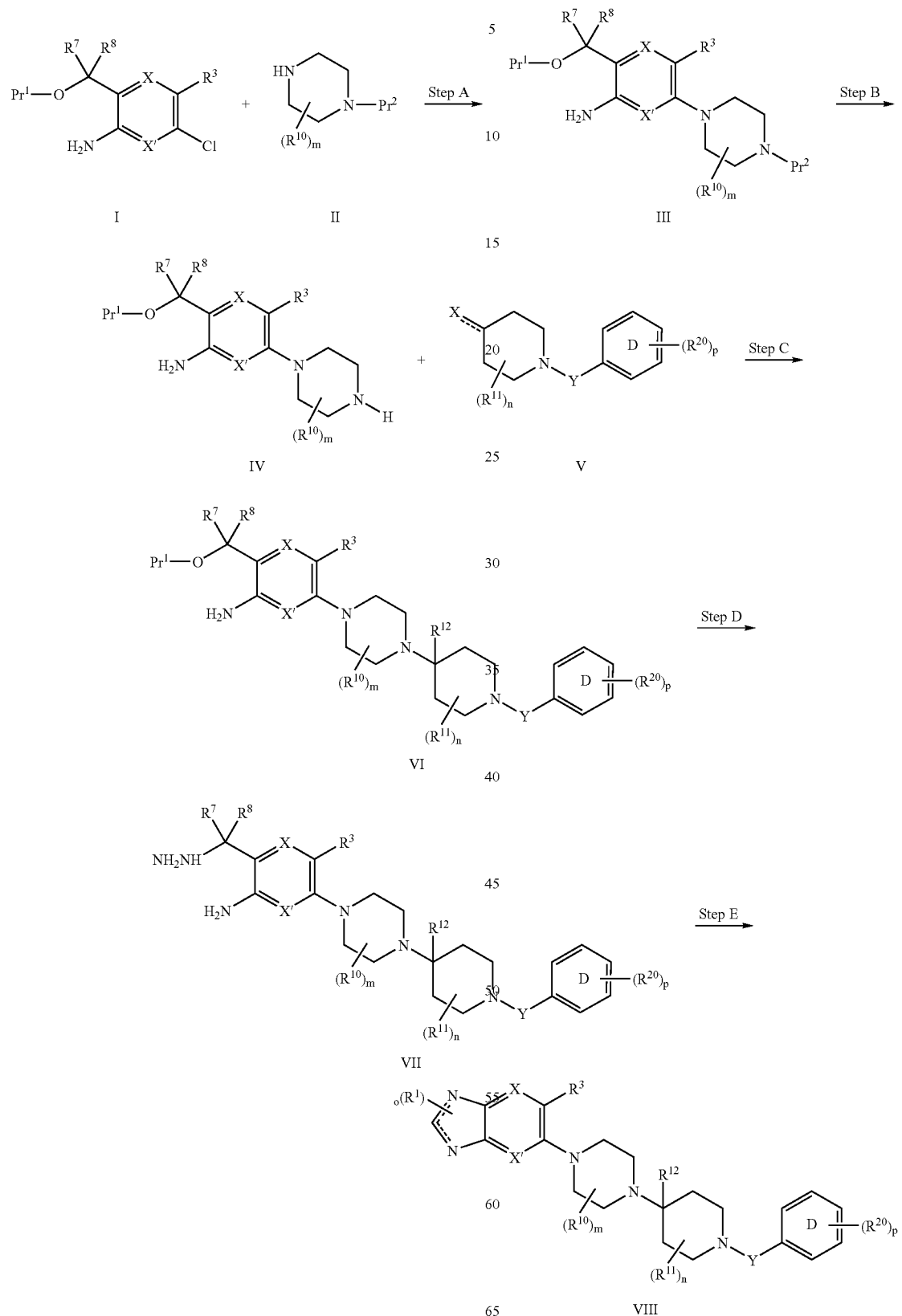

Scheme 2. Method B
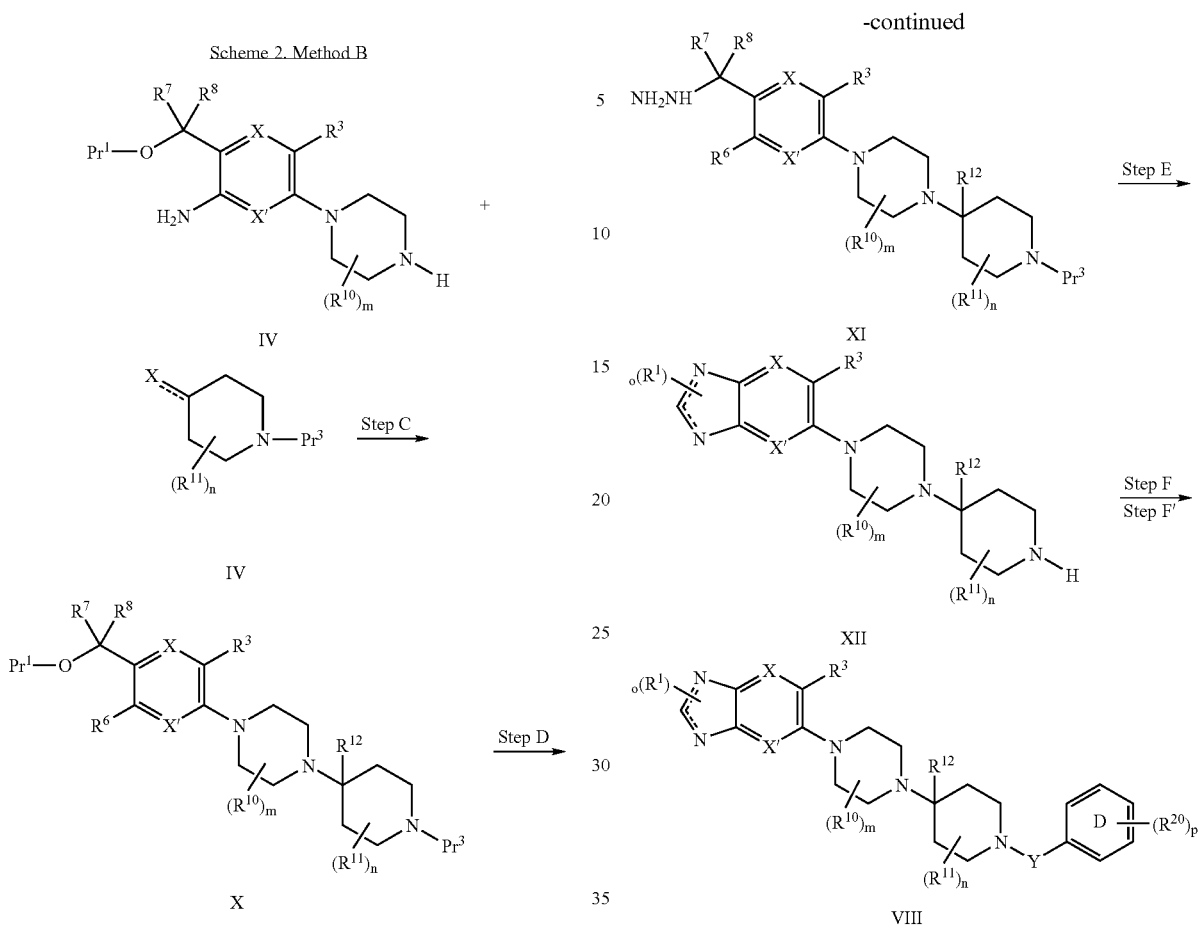
Scheme 3. Method C (Where Z = CR7R8)
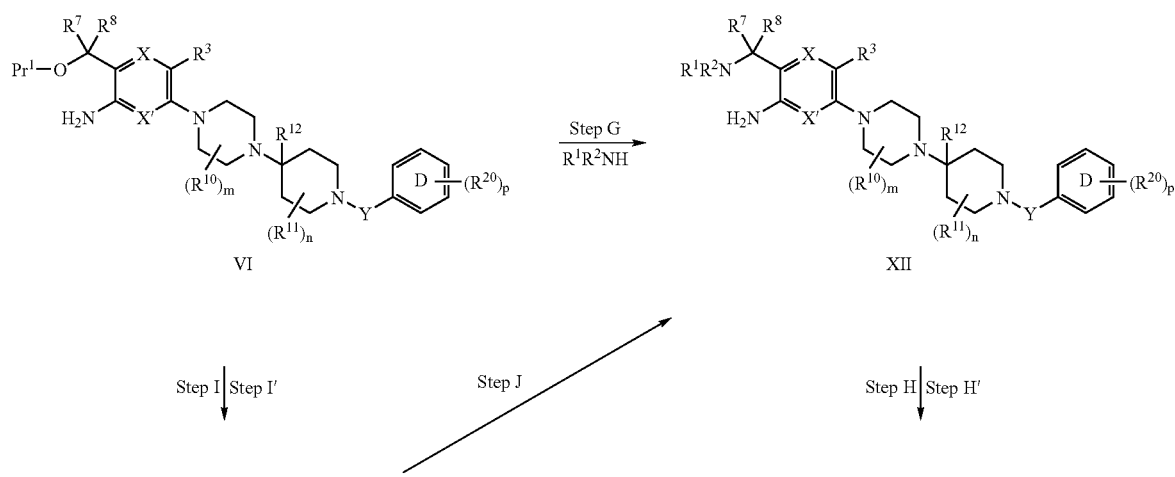

-continued
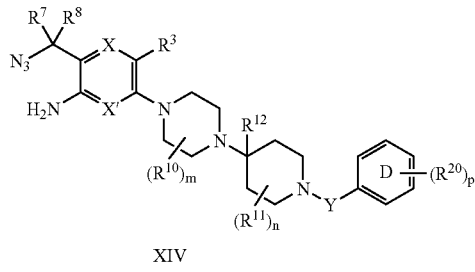
XIV
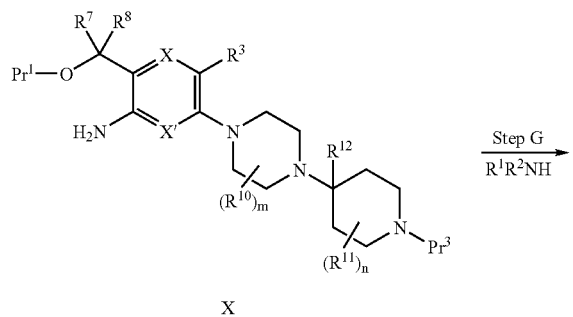
X
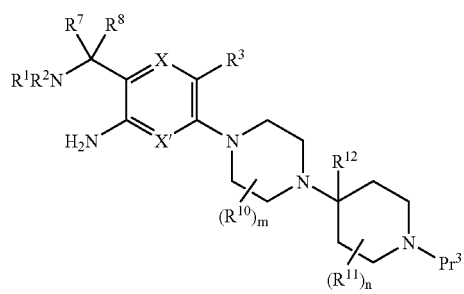
XV
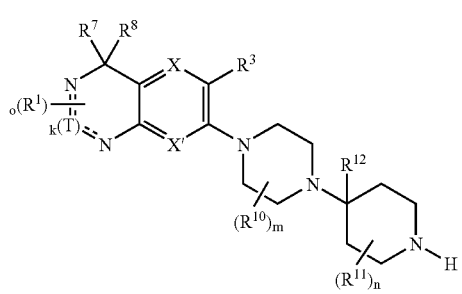
XVI
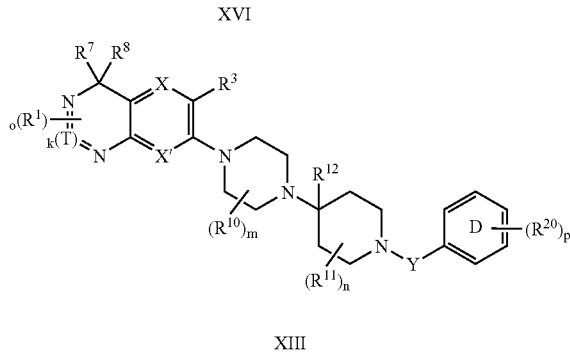
XIII
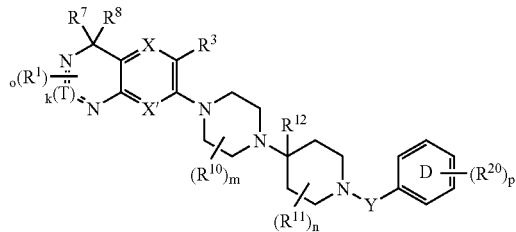
XIII
Scheme 5. Method E (where X = X' = CR⁴)
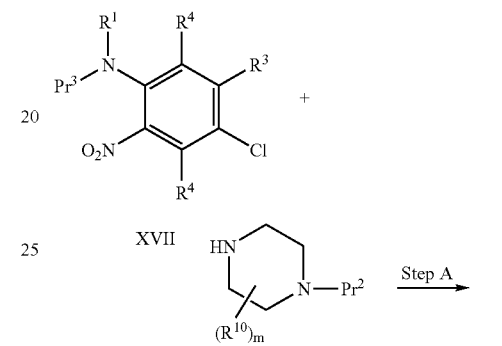
XVII
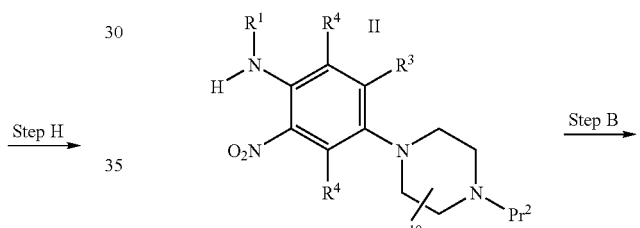
XVIII
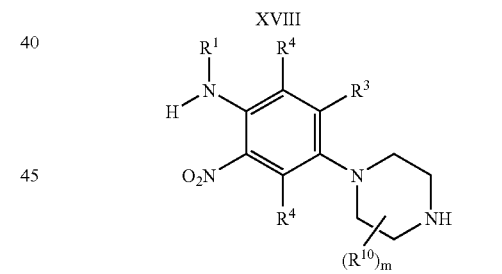
XIX
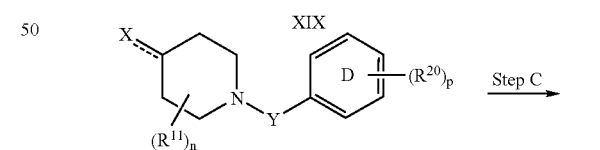
V
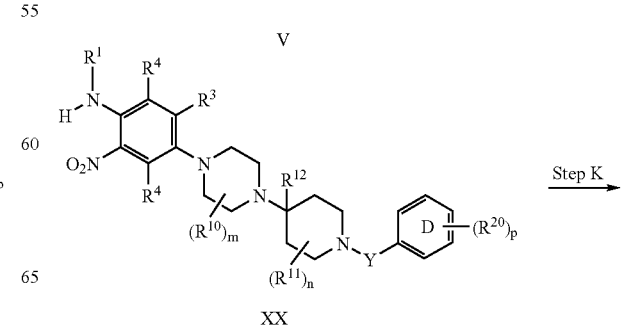
XX

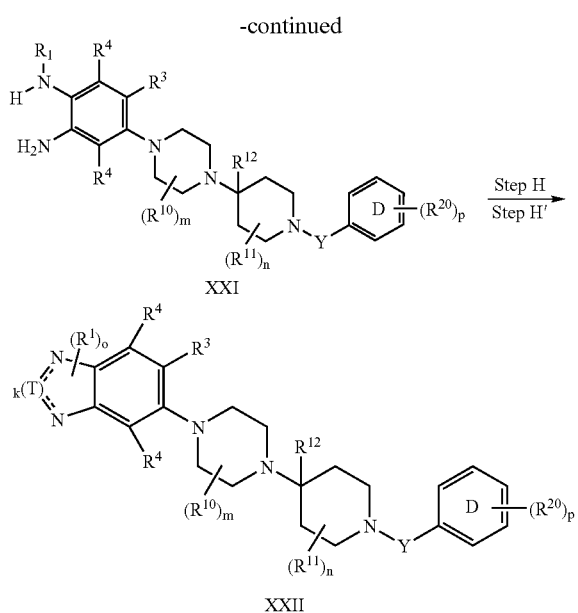

The starting material and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

The preparation of arylpiperazine compounds related to intermediate III has been reported in WO-03037862 (Nippon Shinyaku).

One skilled in the art will recognize that the synthesis of compounds of Formula 1 may require the need for the protection of certain functional groups (i.e. derivatization for the purpose of chemical compatibility with a particular reaction condition). A suitable protecting group for a carboxylic acid ($Pr^1$, when R29 and $R^8$ taken together is =O) is methyl, ethyl, isopropyl, or benzyl ester and the like. A suitable protecting group for an amine ($Pr^2$, $Pr^3$) is methyl, benzyl, ethoxycarbonyl, t-butoxycarbonyl, phthaloyl, trifluoroacetyl, acetyl and the like. All protecting groups can be appended to and removed by literature methods known to those skilled in the art.

One skilled in the art will recognize that the synthesis of compounds of Formula 1 may require the construction of an amide bond. Methods include but are not limited to the use of a reactive carboxyl derivative (e.g. acid halide, or ester at elevated temperatures) or the use of an acid with coupling reagents (e.g. EDCl, DCC, HATU) in the presence of an amine at 0° C. to 100° C. Suitable solvents for the reaction are halogenated hydrocarbons, ethereal solvents, N,N-dimethylformamide and the like. The reaction may be conducted under pressure or in a sealed vessel.

One skilled in the art will recognize that the synthesis of compounds of Formula 1 may require the construction of an amine bond. One such method is, but not limited to, the reaction of a primary or secondary amine with a reactive carbonyl (e.g. aldehyde or ketone) under reductive amination conditions. Suitable reducing agents of the intermediate imine are sodium borohydride, sodium triacetoxyborohydride and the like at 0° C. to 100° C. Suitable solvents for the reaction are halogenated hydrocarbons, ethereal solvents, N,N-dimethylformamide and the like. Another such method is but not limited to the reaction of a primary or secondary amine with a reactive alkylating agent such as an alkyl halide, benzyl halide, mesylate, tosylate and the like. Suitable solvents for the reaction are halogenated hydrocarbons, ethereal solvents, N,N-dimethylformamide and the like. The reaction may be conducted under pressure or in a sealed vessel at 0° C. to 100° C.

One skilled in the art will recognize that the synthesis of compounds of Formula 1 may require the reduction of a reducible functional group. Suitable reducing agents include sodium borohydride, lithium aluminum hydride, diborane and the like at –20° C. to 100° C. Suitable solvents for the reaction are halogenated hydrocarbons, ethereal solvents, N,N-dimethylformamide and the like.

One skilled in the art will recognize that the synthesis of compounds of Formula 1 may require the oxidation of a functional group. Suitable oxidizing reagents include oxygen, hydrogen peroxide, m-chloroperoxybenzoic acid and the like at –20° C. to 100° C. Suitable solvents for the reaction are halogenated hydrocarbons, ethereal solvents, water and the like.

One skilled in the art will note that compounds of Formula 1 require the construction of a heterocyclic ring. Numerous reviews of methodology for the construction of specific heterocyclic systems are in the open literature. In addition to the open literature, monographs and compendiums such as "Comprehensive Heterocyclic Synthesis" (Pergamon Press) are available. Shown below is only one such general methodology for the title compounds.

The starting materials and the intermediates of a reaction may be isolated and purified if desired using conventional techniques, including but not limited to filtration, distillation, crystallization, chromatography and the like. Such materials can be characterized using conventional means, including physical constants and spectral data.

General Description of Methods

Step A. Amination of Pyrazine Ring

A suitably protected 2-halopyrazine of structure I or structure XVII is reacted with a piperazine of structure II to form a compound of structure III or structure XVIII. Preferably the reaction is carried out in a solvent such as dioxane in the presence of a base such as potassium carbonate or cesium carbonate. Optionally, a catalyst such as palladium acetate may be added and the reaction heated to a temperature between 30° C. to 150° C.

Alternatively, other leaving groups may replace the chlorine (O-mesyl, Br etc.) or a group capable of activation under the reaction conditions (H, OH, etc.) may be used.

Step B. Deprotection of Amine Protecting Group

Optionally, if the product of step A is a protected piperazine of structure III or structure XVIII, deprotection is required. When $Pr^2$ is benzyl or substituted benzyl deprotection can be effected by reaction under a pressure of hydrogen gas in the presence of a catalyst such as palladium. When $Pr^2$ is ethoxycarbonyl deprotection can be effected by reaction with trimethylsilyl iodide. When $Pr^2$ is t-butoxycarbonyl deprotection can be effected with a strong acid such as trifluoroacetic acid.

Step C. Reductive Amination

A piperazine of structure IV or XIX is reacted with a compound of structure V or IX in the presence of a reducing agent with or without titanium tetraisopropoxide to form a compound of structure VI, X or XX where $R^{12}$ is hydrogen.

One variation to afford compounds of structure V or 1x with $R^{12}$=CN, is the reaction in the presence of a reducing agent with or without titanium tetraisopropoxide and a cyanide source such as dimethylaluminum cyanide.

General conditions for the reductive amination reaction are described above.

Step D. Hydrazide Formation

A compound of structure VI or X (when R29 and $R^8$ taken together is =O) is reacted with excess amount of hydrazine to form a compound of structure VII or XI where $R^{12}$ is a hydrogen. Preferably the reaction is carried out in refluxing solvents such as EtOH or MeOH for 1-8 hours.

Step E. Curtis Reaction

A compound of structure VII or XI is reacted with reagent such as isoamyl nitrite in the presence of acid to form a reactive intermediate isocyanate, which is followed by intramolecular cyclization to form a compound of structure VIII or XII where $R^{12}$ is hydrogen.

Step F. Appending Ring D

A compound of structure XII or XVI is reacted with a reactive carboxyl derivatives (acid halide or ester) or the corresponding acids under amide coupling conditions to form a compound of general structure VIII or XIII (Y=C=O). Alternatively, a compound of general structure XII can be alkylated to form other compounds of general structure VIII. Alternatively, a compound of structure XII is reacted with reactive carbonyl derivatives (aldehyde or ketone) under the reductive amination condition. Other methods include using alkylating agents such as alkyl halide, benzyl halide, mesylate, tosylate and the like. General conditions are described above.

Step F'.

Optionally, functional group manipulation of a compound of structure VIII may be done to provide additional related compounds of structure VIII.

Step G. Amidation of Ester

A suitable protected ester of structure VI or X where R29 and $R^8$ taken together is =O and $Pr^1$ is alkyl, is reacted with a primary or secondary amine to provide compounds of structure XII or XV. Typical conditions include the reaction of the ester and the amine in a polar solvent such as methanol in a sealed tube at 25° C. to 100° C.

Step I. Reduction of Ester

A suitably protected ester of structure VI where R29 and $R^8$ taken together is =O and $Pr^1$ is alkyl, is reacted with reducing agent such as diisopropyl aluminum hydride to provide a primary hydroxy compound of structure XIV where R29 and $R^8$ are H. General conditions for the reduction are described above.

Step I'. Azide Formation

A primary hydroxy compound of structure VI where $R^1=R^2=H$ is reacted with azide forming agent such as diphenylphosphoryl azide to provide a compound of structure XIV. Typical conditions include that the alcohol is reacted with a base and an azide forming reagent in solvents such as methylene chloride and toluene at 25° C.

Step J. Reduction of Azide

An azide of structure XIV where $R29=R^8=H$ is reduced to amine XII where $R^1=R^2=H$ by hydrogenation in the presence of Pd/C catalyst. The reaction is carried out in the solvents such as MeOH, EtOH or the like at 25° C. under atmospheric pressure.

Step K. Reduction of Nitro Group

A compound of structure XX is reacted with a reducing agent such as sodium borohydride to provide a compound of structure XXI. General conditions for reduction are described above.

Step H. Diamine Cyclization

A compound of structure XII, XV or XXI where $R29=R^8=H$ is reacted with activated carbonyl or activated imine agents to provide the fused bicyclic compounds of structure XIII, XVI or XXII. Typical conditions include the reaction of the diamine and the activated carbonyl agent such as carbonyl diimidazole in a halogenated solvent such as methylene chloride at 25° C. to 100° C.

Step H'

Optionally, functional group manipulation of a compound of structure XII or XXI may be done to provide additional related compounds of structure XIII or XXII.

Compounds of Formula 1 can be prepared by the general methods outlined in Schemes 1, 2, 3, 4, and 5. Synthesis of the specifically exemplified compounds was prepared as described in detailed below. The following EXAMPLES are being provided to further illustrate the present invention. They are for illustrative purposes only; the scope of the invention is not to be considered limited in any way thereby.

EXAMPLES

The following preparative examples are intended to illustrate, but not to limit, the scope of the invention.

Preparative Examples

Preparative Example 1

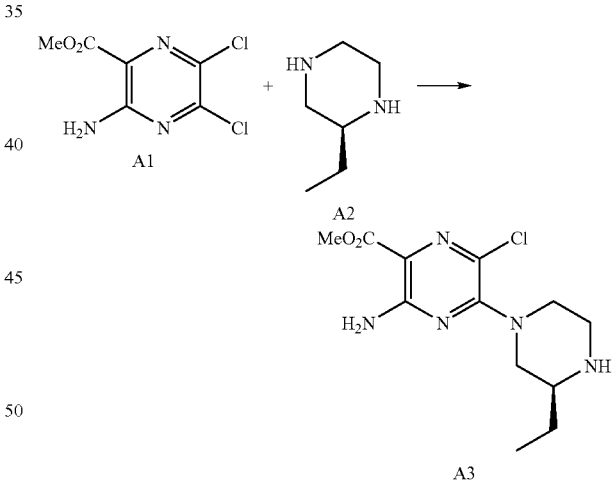

A round bottomed flask was charged with methyl 6-amino 2,3-dichloro pyrazine 5-carboxylate (Aldrich, 25 g, 112.6 mmol), 2-S-ethyl piperazine (prepared as per Williams et al J. Med. Chem 1996, 39, 1345, 83% active, 15.7 g, 112.7 mmol), cesium carbonate (100 g, 300 mmol) and 1,4 dioxane (400 mL). The flask was equipped with a reflux condenser and heated to 80° C. After 12 hours the reaction was cooled, diluted with $CH_2Cl_2$ (~200 mL), and filtered through celite. The filtrate was washed once with water and then concentrated to an oil. The crude product was purified by silica gel column chromatography (3% to 10% MeOH in $CH_2Cl_2$) to afford compound A3 (30.8 g, 91%). MS: M+H=300.

Preparative Example 2

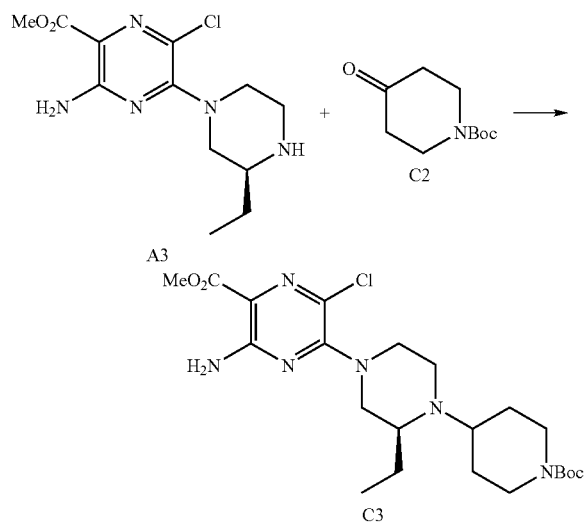

A flask was charged with the compound of structure A3 (6.0 g, 20.0 mmol), N-Boc piperidine-4-one C2 (10.0 g, 50.2 mmol), and 1,2-dichloroethane (100 mL). The reducing reagent NaB(OAc)$_3$H (1.5 equivalents) was added slowly with stirring. The resulting suspension was allowed to stir at 25° C. for 7 days, then treated with 1.0 M sodium solution to pH=13, extracted with CH$_2$Cl$_2$, and dried over sodium sulfate. The solvent was then removed under reduced pressure and the residue was purified by SiO$_2$ column chromatography (1.5% then 5.0% MeOH in CH$_2$Cl$_2$) to provide C3 as a gel (9.8 g, ~100%). MS: M+H=483.

Preparative Example 3

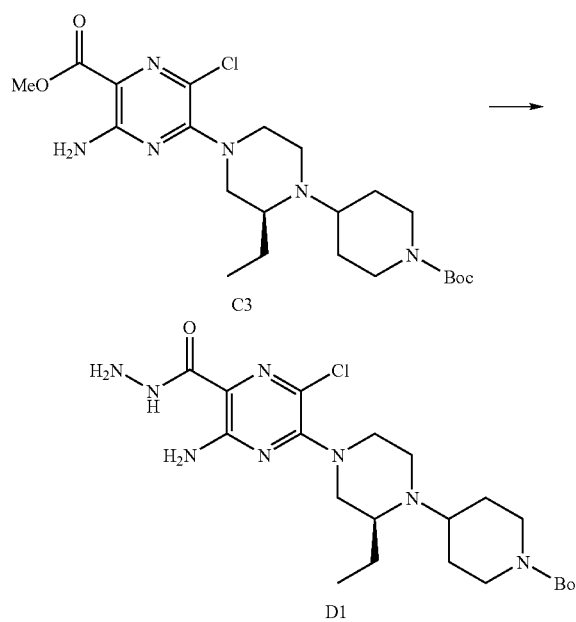

A solution of C3 (5 g, 10.3 mmol) in ethanol (100 mL) was treated with Hydrazine (anhydrous, 4 ml, 127 mmol) at 25° C., and the reaction mixture was stirred at reflux for 22 hours. The reaction mixture was cooled and concentrated in vacuo to provide crude D1. Further purification was carried out using SiO$_2$ flash column chromatography (5% MeOH in CH$_2$Cl$_2$) to afford the desired product D1 (3.06 g, 61% yield). MS: M+H=483.

Preparative Example 4

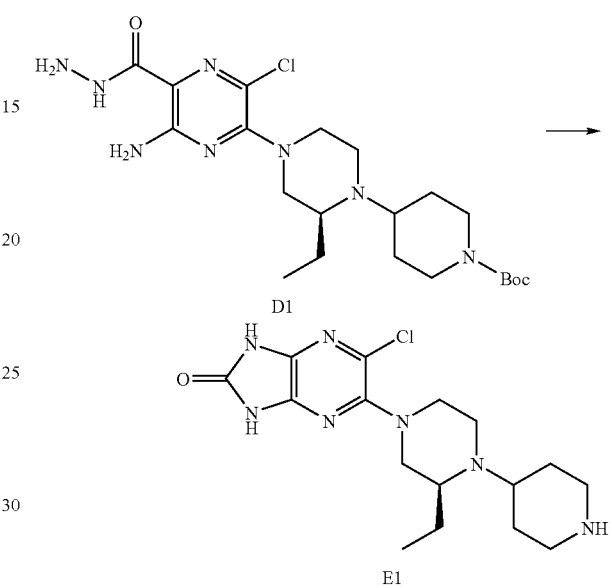

A solution of D1 (1.2 g, 2.5 mmol) in 2-methoxyethanol (32 mL) was treated with 6 N HCl in isopropyl alcohol (1.6 mL) and isoamyl nitrite (0.35 ml, 2.6 mmol) at 25° C. The reaction mixture was stirred for 0.5 hours at the temperature and then heated up to 100° C. for 16 hours. The reaction mixture was cooled and concentrated in vacuo to afford (1.1 g, 91%) of crude product E1 as a HCl salt form which was used for next reaction without further purification. MS: M+H=366 (for free base).

Preparative Example 5

Preparation of Table 1 Compound No. 12

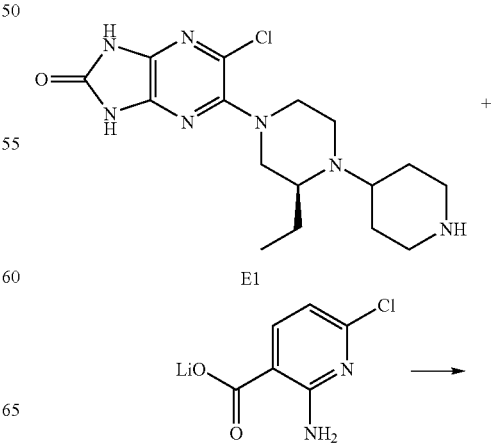

-continued

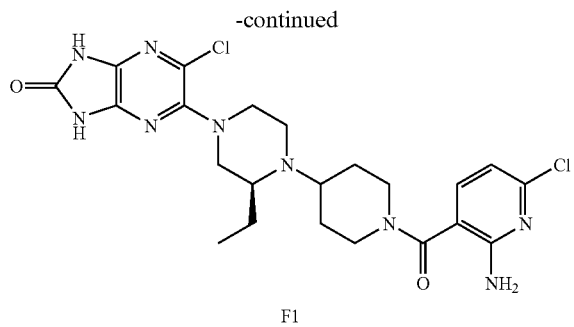

F1

A solution of E1 (hydrochloride salt, 30 mg, 0.074 mmol) in DMF (1 mL) was treated with lithium 2-amino-6-chloronicotinate (15 mg, 0.082 mmol, preparation: see below), 1-[3-(dimethylamino)propyl]-3-ethylcarbodiimide hydrochloride (EDCl, 28 mg, 0.15 mmol), and 1-hydroxybenzotriazole (30 mg, 0.22 mmol) at 0° C. The reaction mixture was allowed to warm up to 25° C. and stirred at the temperature for 16 hours. The reaction mixture was diluted in EtOAc and washed with water. The organic solution was washed with saturated aqueous NaHCO$_3$ solution, brine solution and dried over anhydrous sodium sulfate. After concentration, the residual material was purified by SiO$_2$ column chromatography to afford the desired product F1 (14.7 mg, 38%). MS: M+H=520.

Preparative Example 6

Preparation of Table 1 Compound No. 13

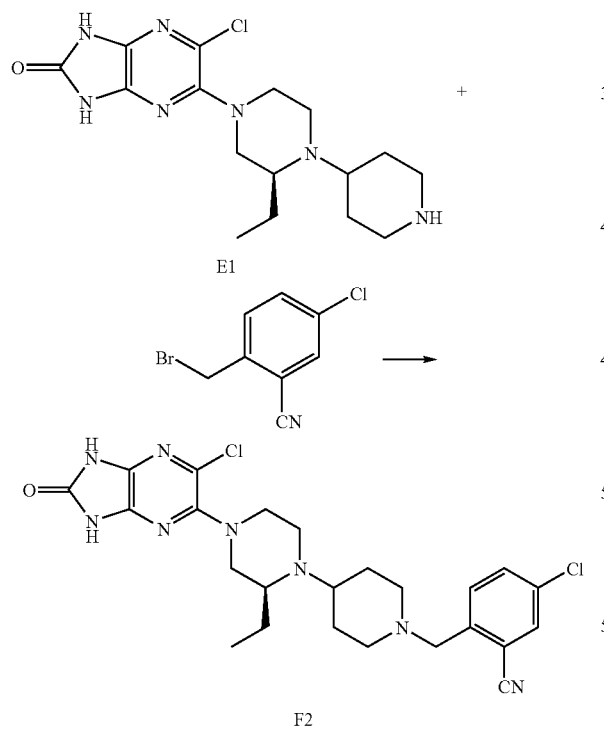

F2

A mixture of E1 (hydrochloride salt form, 100 mg, 0.25 mmol) and sodium iodide (4 mg, 0.025 mmol) in DMF (1 mL) was treated with triethylamine (0.1 ml, 0.75 mmol) and 2-cyano-4-chlorobenzyl bromide (0.11 ml, 0.5 mmol) at 25° C. The reaction mixture was stirred for 3 hours at the temperature and diluted in CH$_2$Cl$_2$. The organic solution was washed with saturated aqueous NaHCO$_3$ solution, brine solution, dried over sodium sulfate, and concentrated in vacuo. The residual material was purified by preparative TLC (10% MeOH in CH$_2$Cl$_2$) to afford the desired product F2 (45 mg, 35%). MS: M+H=517.

Preparative Example 7

Preparation of Table 1 Compound No. 33

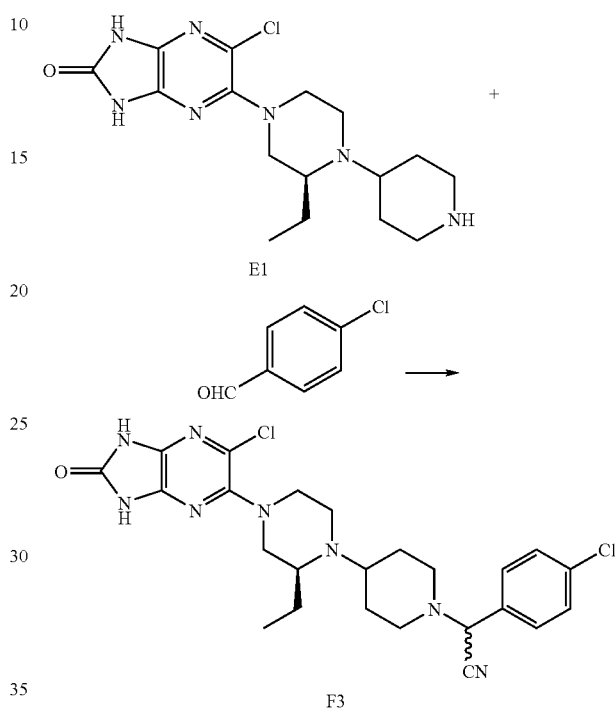

F3

A solution of E1 (hydrochloride salt form, 172 mg, 0.43 mmol) and potassium cyanide (56 mg, 0.86 mmol) in water (1 mL) was treated with 2-3 drops of 1 N HCl at 25° C. The solution was slowly added to a solution of 4-chlorobenzaldehyde in CH$_2$Cl$_2$ (1 mL) at 0° C. The reaction mixture was diluted with methanol (2 mL) and stirred at 25° C. for 4 days. The reaction mixture was poured into water and the organic layers were extracted with EtOAc. The combined organic solution was washed with brine solution, dried over sodium sulfate, and concentrated in vacuo. The residual material was purified by preparative TLC (10% MeOH in CH$_2$Cl$_2$) to afford the desired product F3 (117 mg, 53%) as a 1:1 mixture of diastereoisomers. MS: M+H=515.

Preparative Example 8

Preparation of Table 1 Compound No. 2

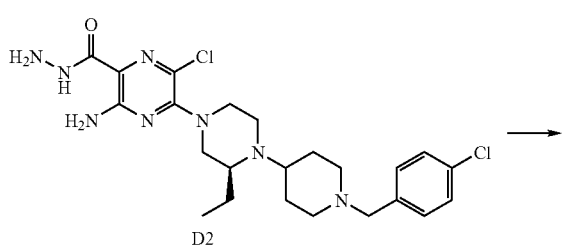

D2

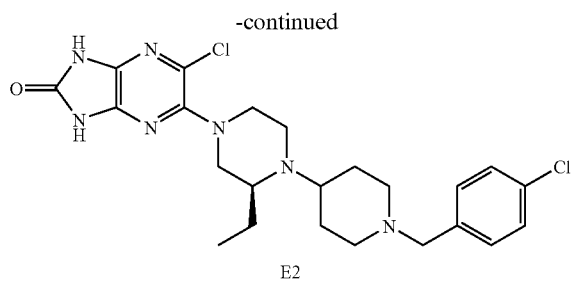

E2

A solution of D2 (82 mg, 0.16 mmol) in 2-methoxyethanol (2 mL) was treated with 6 N HCl in isopropyl alcohol (0.1 mL) and isoamyl nitrite (23 μl, 0.17 mmol) at 25° C. The reaction mixture was stirred for 0.5 hours at the temperature and then heated up to 100° C. for 16 hours. The reaction mixture was cooled and concentrated in vacuo to afford the desired product E2 (82 mg, 98%) as a HCl salt form which was pure enough without further purification. MS: M+H=490 (for free base).

Preparative Example 9

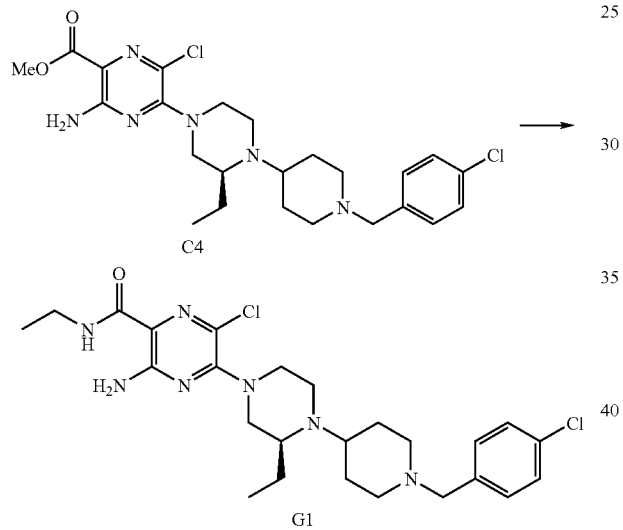

An ester of structure C4 (20 mg, 0.04 mmol) was dissolved in 2 N ethyl amine in MeOH (5 mL). The reaction mixture was heated to 65° C. for 18 hours in a pressure vessel. The reaction mixture was cooled and concentrated in vacuo. The residual material was purified by $SiO_2$ column chromatography (3% to 10% MeOH in $CH_2Cl_2$) to afford the desired product G1 (18 mg, 88%). MS: M+H=520.

Preparative Example 10

Preparation of Table 1 Compound No. 20

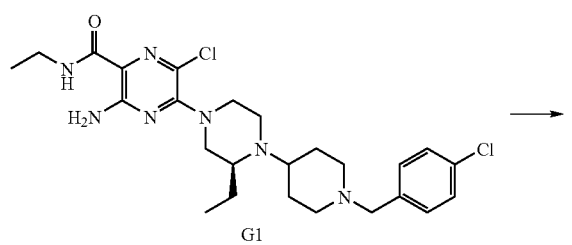

G1

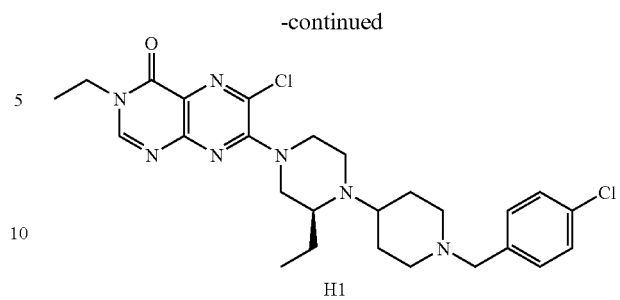

H1

A compound of structure of G1 (12 mg, 0.023 mmol) was dissolved in ethyl orthoformate (1 mL) and acetic anhydride (1 mL). The reaction mixture was stirred at 100° C. for 16 hours. The reaction mixture was cooled and concentrated in vacuo. The residual material was dissolved in $CH_2Cl_2$ and the organic solution was washed with saturated aqueous $NaHCO_3$ solution, brine solution, dried over sodium sulfate, and concentrated in vacuo. Purification by preparative TLC (10% MeOH in $CH_2Cl_2$) afforded the desired product H1 (6 mg, 50%). MS: M+H=530.

Preparative Example 11

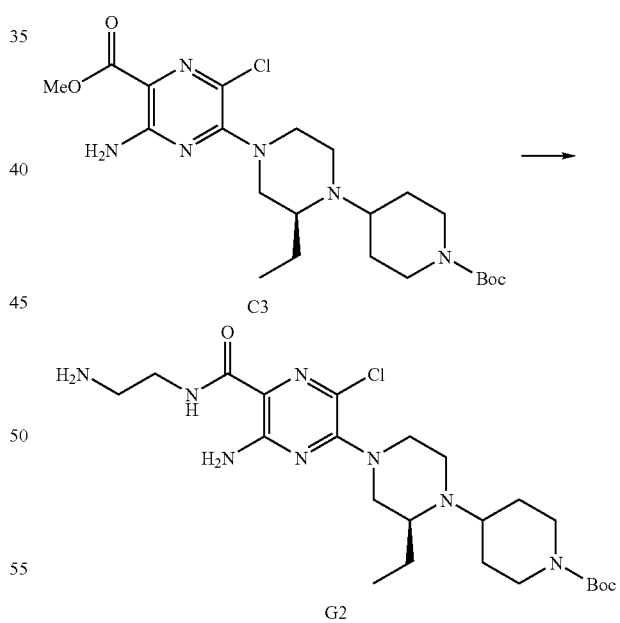

A solution of compound C3 (0.75 g, 1.55 mmol) in MeOH (10 mL) was treated with ethylene diamine (1.57 ml, 233 mmol) at 25° C. The reaction mixture was stirred at 70° C. for 16 hours in a sealed tube. The reaction mixture was cooled and concentrated in vacuo. The residual material was purified by $SiO_2$ column chromatography (2% MeOH in $CH_2Cl_2$ to a mixture of CH₂Cl₂/MeOH/NH₄OH, 94/5/1) to afford the desired product G2 (510 mg, 64%). MS: M+H=511.

Preparative Example 12

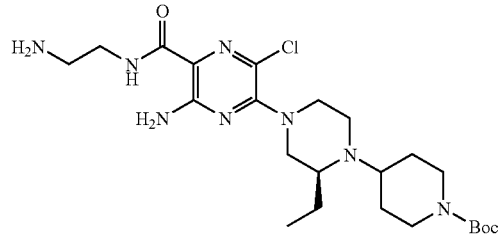
G2

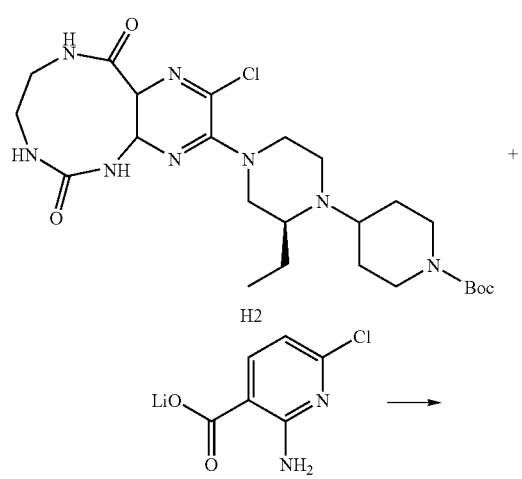
H2

A solution of compound G2 (175 mg, 0.34 mmol) in CHCl₃ (2 mL) was treated with carbonyl diimidazole (61 mg, 0.37 mmol) at 25° C. The reaction mixture was stirred at the temperature for 16 hours. The reaction mixture was concentrated in vacuo and the residual material was dissolved in CH₂Cl₂ (5 mL). The solution was treated with trifluoroacetic acid (0.5 mL) at 0° C., and the reaction mixture was stirred for 3 hours at 25° C. The reaction mixture was concentrated in vacuo and the residual material was purified by SiO₂ column chromatography (CH₂Cl₂/MeOH/NH₄OH=93/5/2 to 88/10/2) to afford the desired product H2 (33 mg, 22%). MS: M+H=437.

Preparative Example 13

Preparation of Table 1 Compound No. 34

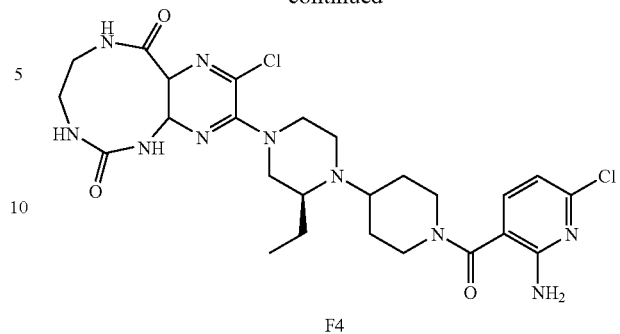
F4

A solution of H2 (30 mg, 0.068 mmol) in DMF (2 mL) was treated with lithium 2-amino-6chloronicotinate (18 mg, 0.102 mmol, preparation: see below), O-(7-Azabenzotriazol-1-yl)-N,N,N',N'-tetramethyluronium hexafluorophosphate (HATU, 38 mg, 0.10 mmol), and triethylamine (95 μl, 0.68 mmol) at 25° C. The reaction mixture was stirred at the temperature for 16 hours. The reaction mixture was diluted in EtOAc and washed with water. The organic solution was washed with brine solution and dried over anhydrous sodium sulfate. After concentration, the residual material was purified by preparative TLC (CH₂Cl₂/MeOH/NH₄OH=93/5/2) to afford the desired product F4 (3.5 mg, 8.8%). MS: M+H=591.

Preparative Example 14

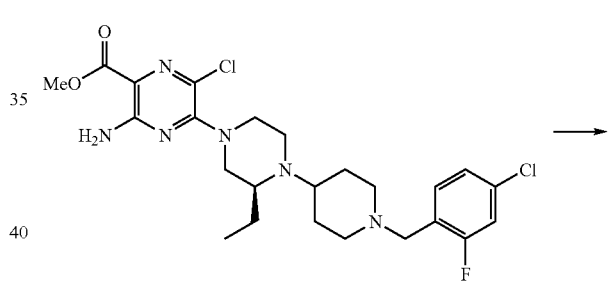
C5

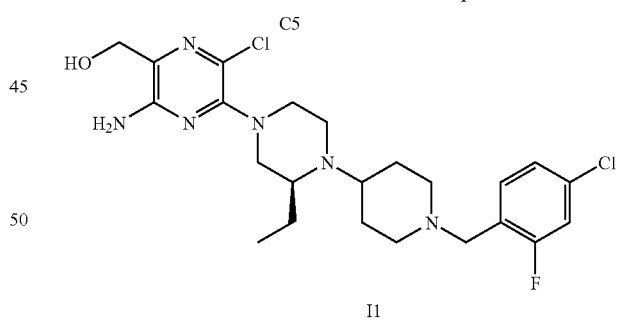
I1

Compound C5 (1.74 g, 3.30 mmol) was dissolved in anhydrous THF (30 mL) and was cooled to −78° C. with a dry ice acetone bath. DIBAL (1 M, 11.6 ml, 11.6 mmol) was added dropwise through a syringe. After the reaction mixture was stirred at −78° C. for 1 hour, saturated aqueous sodium potassium tartrate solution was added. The reaction mixture was allowed to warm up to 25° C. and stirred for 0.3 hours. The aqueous layer was extracted with EtOAc. The organic solution was dried over anhydrous sodium sulfate, filtered, and concentrated to dryness. The crude product was purified by silica gel chromatography (5% MeOH in CH₂Cl₂) to give the desired compound I1 (1.40 g, 85%). MS: M+H=497.

Preparative Example 15

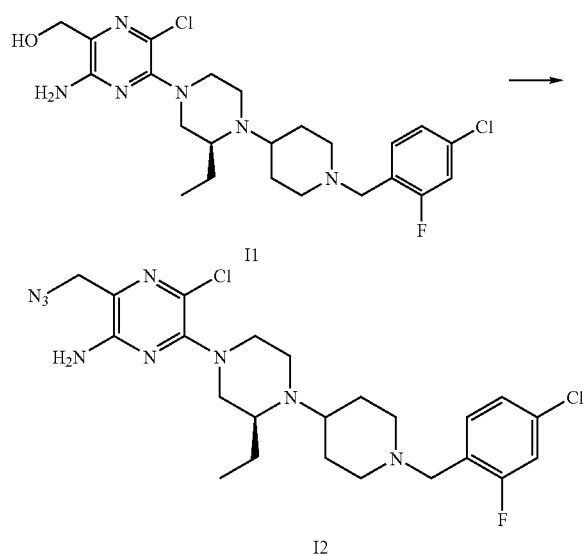

Compound I1 (210 mg, 0.422 mmol) was dissolved in a mixture of anhydrous $CH_2Cl_2$ and anhydrous toluene (1:1, 7 mL). Diphenylphosphoryl azide (0.096 ml, 0.443 mmol) and 1,8-diazabicyclo[5.4.0]undec-7-ene (DBU, 0.070 ml, 0.464 mmol) was added. After the reaction mixture was stirred at 25° C. for 12 hours, it was concentrated to dryness. The crude product was purified by silica gel column chromatography (2.5% MeOH in $CH_2Cl_2$) to give compound 12 (170 mg, 77%). MS: M+H=522.

Preparative Example 16

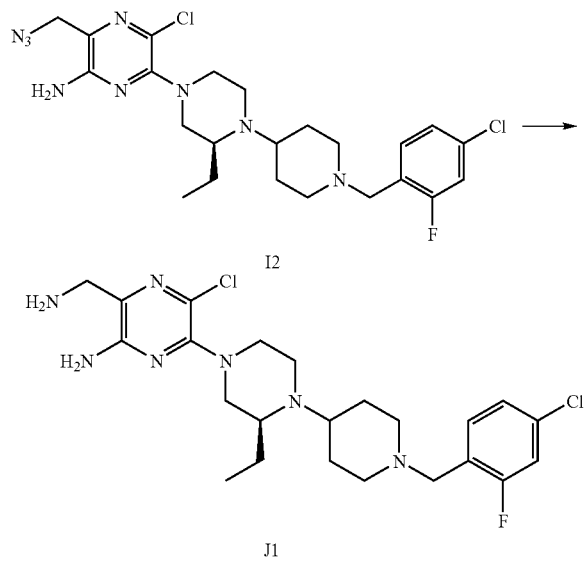

Compound I2 (170 mg, 0.325 mmol) and triphenylphosphine (110 mg, 0.422 mmol) were dissolved in THF (2 mL). Water (5 drops) was added. The reaction mixture was stirred at 25° C. 16 hours. The reaction mixture was concentrated in vacuo. The crude product was purified by silica gel column chromatography (5% MeOH in $CH_2Cl_2$) to afford the desired compound J1 (156 mg, 97%). MS: M+H=496

Preparative Example 17

Preparation of Table 1 Compound No. 4

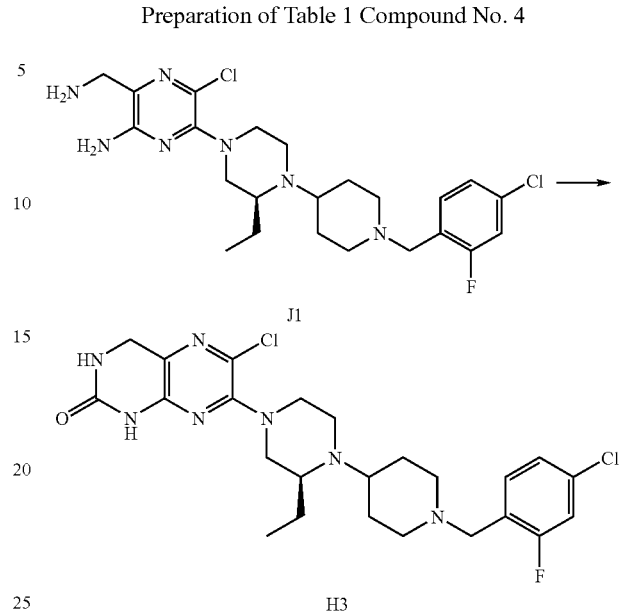

Compound J1 (48.0 mg, 0.097 mmol) and N,N'-carbonyl diimidazole (16 mg, 0.097 mmol) were dissolved in $CHCl_3$ (1 mL). After the reaction mixture was stirred at 25° C. for 10 minutes, it was heated to reflux for 2 hours. After cooling, the solvent was concentrated to dryness, and the crude product was purified by silica gel column chromatography (2.5% MeOH in $CH_2Cl_2$) to give the desired compound H3 (40 mg, 79%). MS: M+H=522.

Preparative Example 18

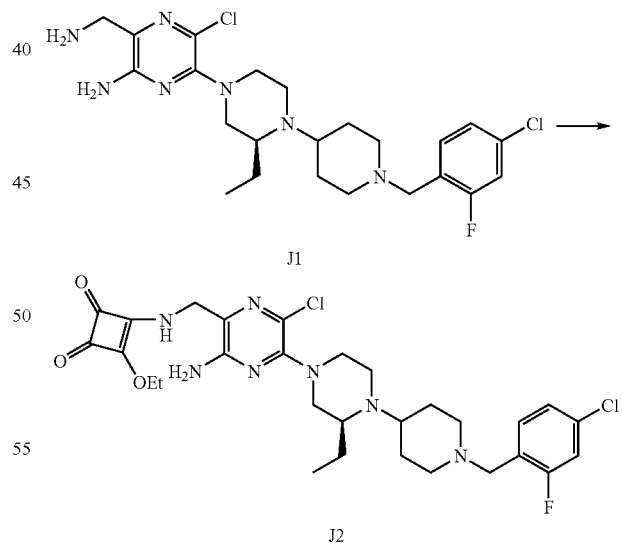

Compound J1 (82.5 mg, 0.177 mmol) and 3,4-diethoxy-3-cyclobutene-1,2-dione (30.7 mg, 0.177 mmol) were dissolved in EtOH (2 mL). The reaction mixture was stirred at 25° C. for 12 hours. The solvent was evaporated to dryness and, the crude product was purified by silica gel column chromatography (2.5% MeOH in $CH_2Cl_2$) to give the desired compound J2 (80.8 mg, 75%). MS: M+H=620

Preparative Example 19

Preparation of Table 1 Compound No. 1

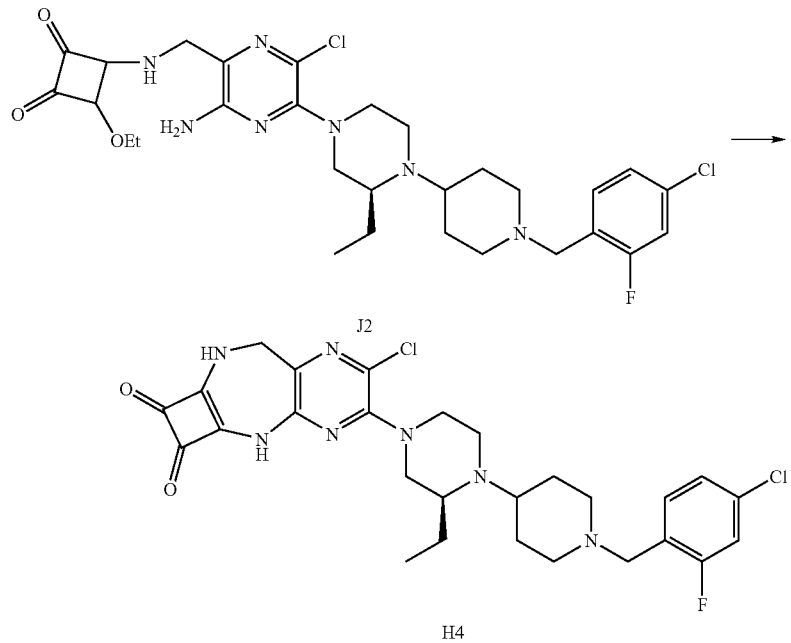

Compound J2 (16 mg, 0.025 mmol), N,N-diisopropylethylamine (2 drop) and EtOH were added to a pressure tube. The tube was sealed and heated to 130° C. for 2 days. After cooling, the solvent was concentrated to dryness. The crude product was purified by preparative TLC (5% MeOH in $CH_2Cl_2$) to give the desired compound H4 (3.8 mg, 26%). MS: M+H=574.

Preparative Example 20

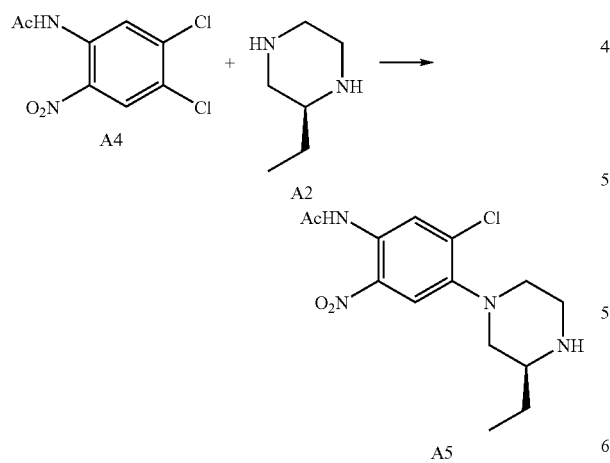

The commercially available N-(4,5-Dichloro-2-nitro-phenyl)-acetamide A4 (1.4 g, 5.6 mmol) was mixed with (S)-ethylpiperazine HCl salt A2 (1 g, 4.7 mmol), $K_2CO_3$ (5 g, 37 mmol), catalytic KI in N,N-dimethylformamide. The mixture was heated at 90° C. for 16 hours and solvent was removed. After aqueous workup, the crude product was purified by silica gel column chromatography to afford the desired product A5 (1.03 g, 79%). MS: M+H=327.

Preparative Example 21

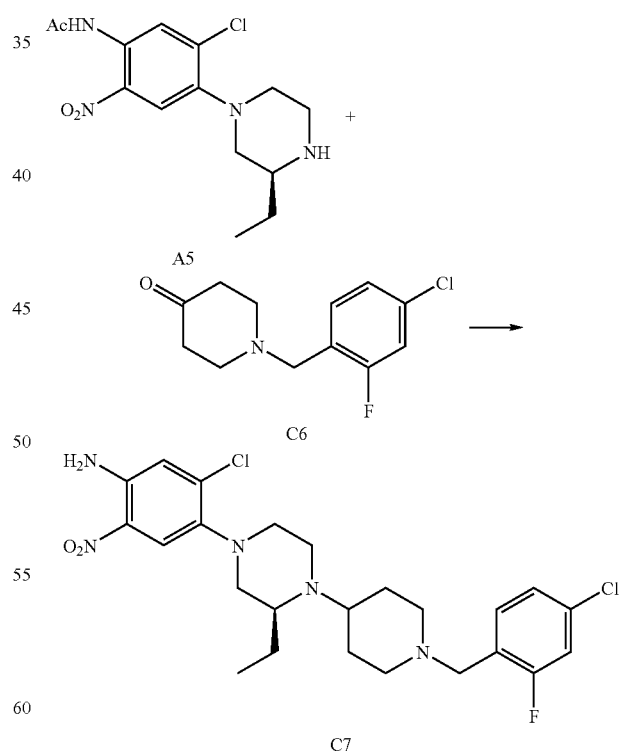

A compound of structure A5 (500 mg, 1.53 mmol) and 1-(4-Chloro-2-fluoro-benzyl)-piperidin-4-one C6 were dissolved in 3% HOAc/DMF and sodium triacetoxyborohydride (650 mg, 3 mmol) was added. The reaction mixture was stirred for 16 hours at 25° C. After aqueous workup, the crude product was purified by silica gel column chromatography to yield the desired compound C7 (750 mg, 96%). MS: M+H=510.

Preparative Example 22

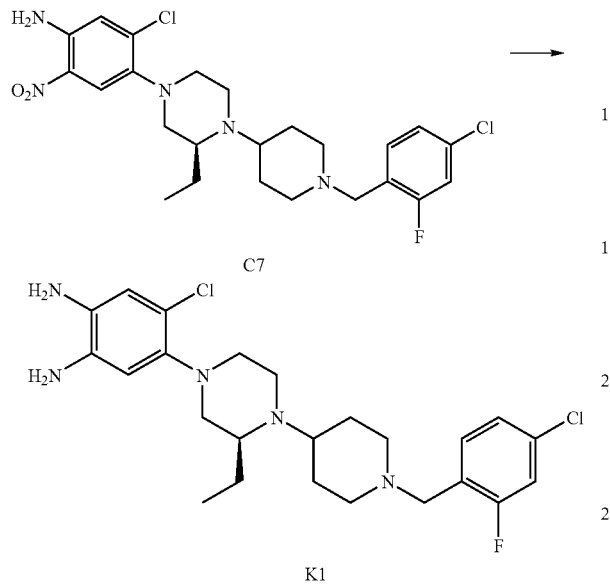

A compound of structure C7 (330 mg, 0.65 mmol) was dissolved in absolute EtOH. Sodium borohydride (123 mg, 3.25 mmol) and cobalt chloride (85 mg, 0.65 mmol) was slowly added and the mixture was heated at 85° C. for 45 minutes. The reaction was then quenched by water. After aqueous workup, the crude product was purified by silica gel column chromatography to give the desired product K1 (260 mg, 83%). MS: M+H=480.

Preparative Example 23

Preparation of Table 1 Compound No. 10

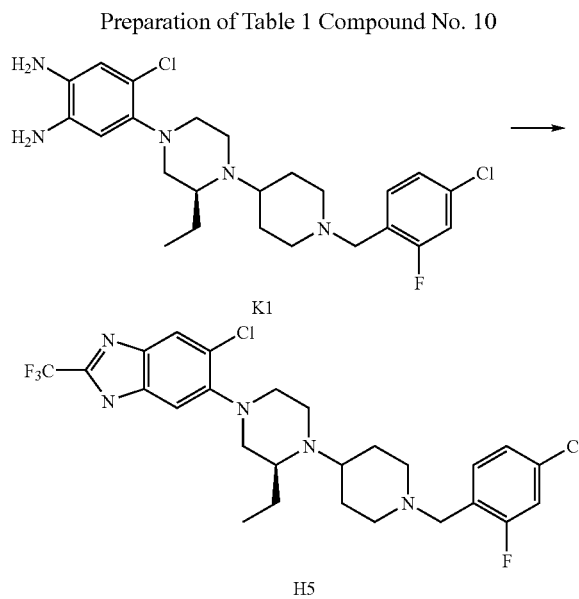

A compound of structure K1 (10 mg, 0.02 mmol) and 1 ml of trifluoroacetic acid were added in a pressure vessel and the reaction mixture was heated at 90° C. for 16 hours. Solvent was removed and the crude product was purified by preparative HPLC to yield the desired compound H5 (8 mg, 73%). MS: M+1=558.

Preparative Example 24

Preparation of Table 1 Compound No. 21

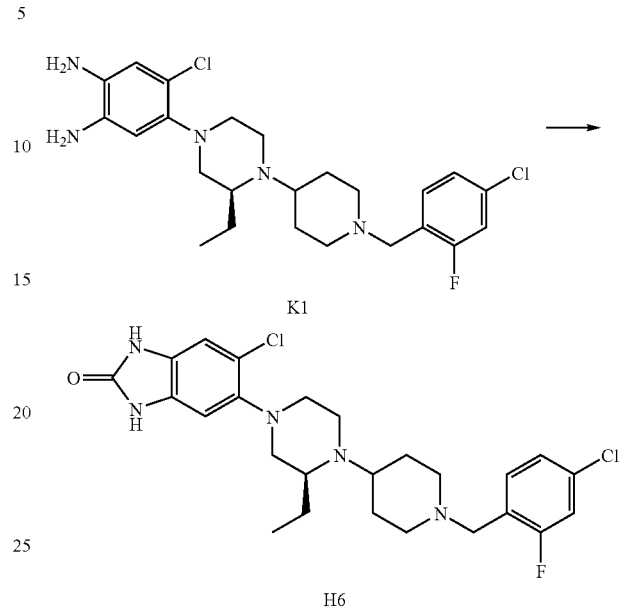

A compound of structure K1 (8.4 mg, 0.018 mmol) was dissolved in THF (1 mL). 1,1'-carbonyldiimidazole (20 mg, 0.12 mmol) and triethylamine (0.1 mL) were added and the reaction mixture was stirred at 25° C. for 16 hours. Solvent was removed and the crude product was purified by preparative HPLC to yield the desired compound H6 (6 mg, 88%). MS: M+H=506, Preparative Example 25

Preparation of Table 1 Compound No. 5

Preparation of Table 1 Compound No. 5 was prepared by the same method shown for Preparative Examples 14 through 17. MS: M+H=547.

Preparative Example 26

Preparation of Table 1 Compound No. 16

Preparation of Table 1 Compound No. 16 was prepared by the same method shown for Preparative Examples 14 through 17. MS: M+H=523.

Preparative Example 27

Preparation of Table 1 Compound No. 3

Preparation of Table 1 Compound No. 3 was prepared by the same method shown for Preparative Examples 3 through 6. MS: M+H=521.

Preparative Example 28

Preparation of Table 1 Compound No. 6

Preparation of Table 1 Compound No. 6 was prepared by the same method shown for Preparative Example 8. MS: M+H=509.

Preparative Example 29

Preparation of Table 1 Compound No. 11

Preparation of Table 1 Compound No. 11 was prepared by the same method shown for Preparative Examples 3 through 6. MS: M+H=521.

Preparative Example 30

T Preparation of Table 1 Compound No. 14

Preparation of Table 1 Compound No. 14 was prepared by the same method shown for Preparative Examples 3 through 6. MS: M+H=549.

Preparative Example 31

Preparation of Table 1 Compound No. 17

Preparation of Table 1 Compound No. 17 was prepared by the same method shown for Preparative Examples 3 through 6. MS: M+H=523.

Preparative Example 32

Preparation of Table 1 Compound No. 7

Preparation of Table 1 Compound No. 7 was prepared by the same method shown for Preparative Examples 9 through 10. MS: M+H=533.

Preparative Example 33

Preparation of Table 1 Compound No. 15

Preparation of Table 1 Compound No. 15 was prepared by the same method shown for Preparative Examples 9 through 10. MS: M+H=577.

Preparative Example 34

Preparation of Table 1 Compound No. 9

Preparation of Table 1 Compound No. 9 was prepared by the same method shown for Preparative Examples 20 through 23. MS: M+H=559.

Lithium 2-amino-5-chloronicotinate

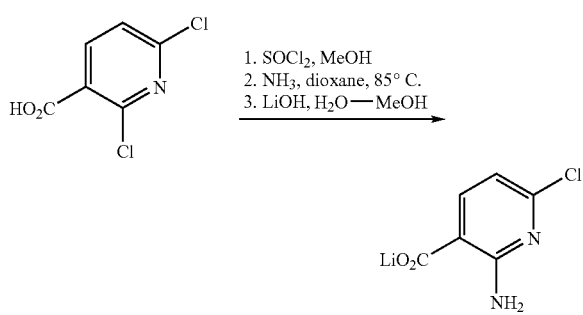

A solution of 2,5-dichloronicotinic acid (20.2 g, 0.105 mol) in methanol (500 mL) was cooled to 0° C. and neat thionyl chloride (38 mL, 63 g, 0.525 mol) was added over ~30 min. The reaction mixture was stirred at 0° C. for 1 hour. The cooling bath was removed, the reaction temperature was allowed to warm to room temperature, and the reaction was allowed to stir for an additional 2 days at room temperature. The solvent was removed under reduced pressure to give an off-white residue. The residue was dissolved in $Et_2O$ (~500 mL) and the resulting solution was washed successively with saturated aqueous $NaHCO_3$ solution (~300 mL), water (~300 mL), and brine (~300 mL). The organic layer was separated, dried over anhydrous $MgSO_4$, and filtered. Removal of the solvent under reduced pressure yielded methyl 2,5-dichloronicotinate (21.0 g, 97%) as a white solid.

Performed in duplicate on identical scales in two pressure vessels, methyl 2,5-dichloronicotinate (4.5 g, 22 mmol) was dissolved in ammonia solution (250 mL, 0.5 M in 1,4-dioxane; 0.125 mol). The pressure vessels were sealed and heated at $(85\pm5)°$ C. for 9 days. The two reaction mixtures were allowed to cool to rt, then combined and concentrated under reduced pressure to yield a white solid. Dissolution of the solid in 1:1 acetone-MeOH (~500 mL), followed by adsorption onto silica gel (25 g) and then purification by flash column chromatography (25:10:1 hexane-$CH_2Cl_2$-$Et_2O$), gave 6.08 g (75%) of methyl 2-amino-5-chloronicotinate.

A solution of $LiOH \cdot H_2O$ (1.38 g, 33 mmol) in water (33 mL) was added in one portion to a suspension of methyl 2-amino-5-chloronicotinate (6.08 g, 27 mmol) in MeOH (110 mL). The reaction mixture was stirred at 70° C. for 24 hours, and gradually became homogeneous. The solvents were removed under reduced pressure, and after the resulting white solid was dried under vacuum (<1 mmHg) to constant weight, 5.51 g (95%) of lithium 2-amino-5-chloronicotinate was obtained.

Biological Examples

The inventive compounds can readily be evaluated to determine activity at the CXCR3 receptors by known methods, such as, for example, development of a human CXCR3 (N-delta 4) Binding Assay.

Cloning and Expression of Human CXCR3 (N-delta 4):

The DNA encoding human CXCR3 was cloned by PCR using human genomic DNA (Promega, Madison, Wis.) as a template. The PCR primers were designed based on the published sequence of human orphan receptor GPR9 (1) with incorporated restriction sites, a Kozak consensus sequence, CD8 leader and Flag tag. The PCR product was subcloned into the mammalian expression vector pME18Sneo, a derivative of the SR-alpha expression vector (designated as pME18Sneo-hCXCR3 (N-delta 4).

IL-3-dependent mouse pro-B cells Ba/F3 were transfected by electroporation in 0.4 ml Dulbecco's PBS containing $4 \times 10^6$ cells with 20 µg of pME18Sneo-hCXCR3 (N-delta 4) plasmid DNA. Cells were pulsed at 400 Volts, 100 OHMs, 960 pFd. The transfected cells were under selection with 1 mg/ml G418 (Life Technologies, Gaithersburg, Md.). G418-resistant Ba/F3 clones were screened for CXCR3 expression by specific binding of [$^{125}$I] IP10 (NEN Life Science Products, Boston, Mass.).

Preparation of Ba/F3-hCXCR3 (N-delta 4) Membranes:

Ba/F3 cells expressing human CXCR3 (N-delta 4) were pelleted and resuspended in the lysis buffer containing 10 mM HEPES, pH 7.5 and Complete® protease inhibitors (1 tablet per 100 ml) (Boehringer Mannheim, Indianapolis, Ind.) at a cell density of $20 \times 10^6$ cells per ml. After 5 minute incubation on ice, cells were transferred to 4639 cell disruption bomb (Parr Instrument, Moline, Ill.) and applied with 1,500 psi of nitrogen for 30 minutes on ice. Large cellular debris was removed by centrifugation at 1,000×g. Cell membrane in the supernatant was sedimented at 100,000×g. The membrane was resuspended in the lysis buffer supplemented with 10% sucrose and stored at −80° C. Total protein concentration of the membrane was determined by BCA method from Pierce (Rockford, Ill.).

Human CXCR3 (N-delta 4) Scintillation Proximity Assay (SPA):

For each assay point, 2 μg of membrane was preincubated for 1 hr with 300 μg wheat germ agglutinin (WGA) coated SPA beads (Amersham, Arlington Heights, Ill.) in the binding buffer (50 mM HEPES, 1 mM $CaCl_2$, 5 mM $MgCl_2$, 125 mM NaCl, 0.002% $NaN_3$, 1.0% BSA) at room temperature. The beads were spun down, washed once, resuspended in the binding buffer and transferred to a 96-well Isoplate (Wallac, Gaithersburg, Md.). 25 pM of [$^{125}$I] IP-10 with tested compounds in a series of titration were added to start the reaction. After 3 hr reaction at room temperature, the amount of [$^{125}$I] IP10 bound to the SPA beads was determined with a Wallac 1450 Microbeta counter.

The Ki ratings for the various compounds of the present invention are given in the afore-mentioned Table 1. From these ratings and value ranges, it would be apparent to the skilled artisan that the compounds of the invention have excellent utility as CXCR3 receptor antagonists.

While the present invention has been describe in conjunction with the specific embodiments set forth above, many alternatives, modifications and variations thereof will be apparent to those of ordinary skill in the art. All such alternatives, medications and variations are intended to fall within the spirit and scope of the present invention.

What is claimed is:

1. A compound selected from the group consisting of:

| Compound Number | STRUCTURE |
|---|---|
| 13 | |
| 14 | |
| 15 | 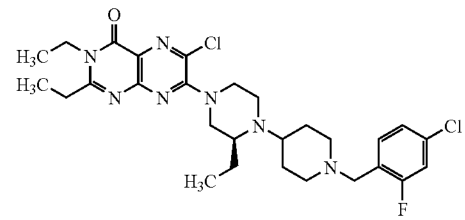 |
| 16 | 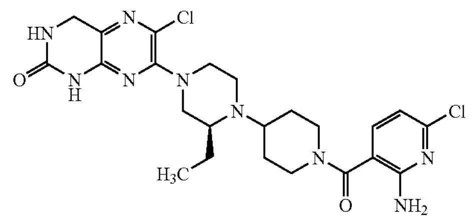 |
| 17 | 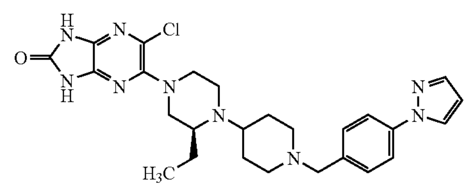 |
| 18 | 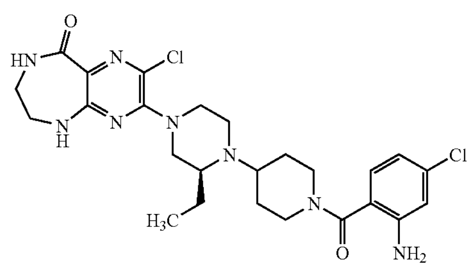 |
| 19 | 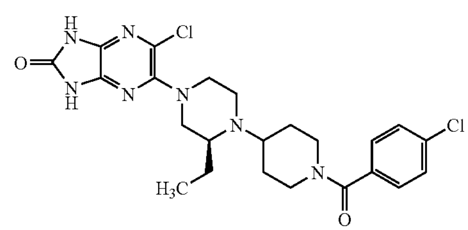 |
| 20 | 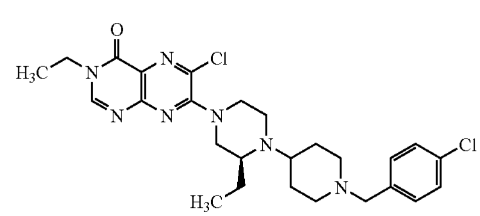 |
| 22 | 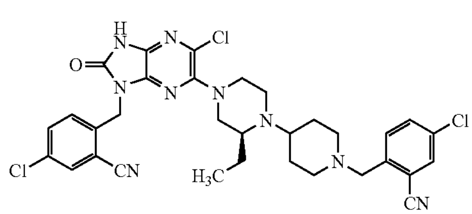 |

-continued
| Compound Number | STRUCTURE |
|---|---|
| 23 | 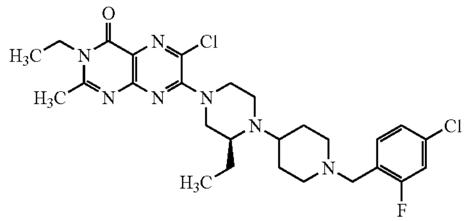 |
| 26 | 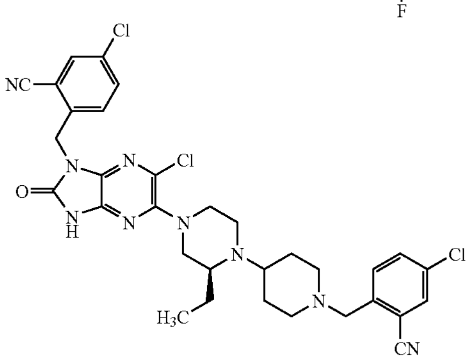 |
| 30 | 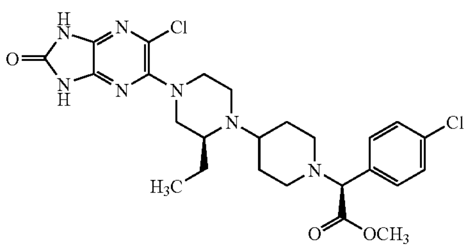 |
| 33 | 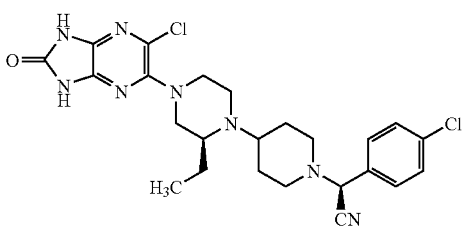 |
| 34 | 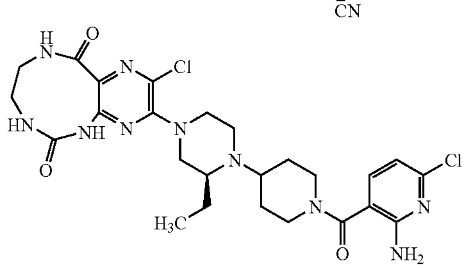 |
| | and |
| 38 | 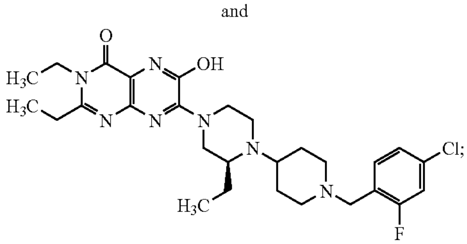 |
or a pharmaceutically acceptable salt thereof.
2. A compound selected from the group consisting of:
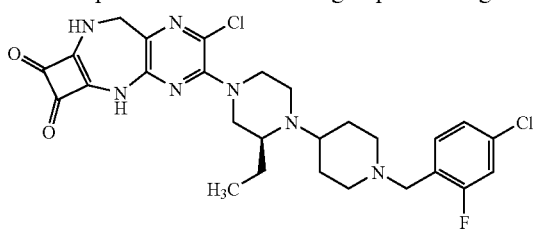
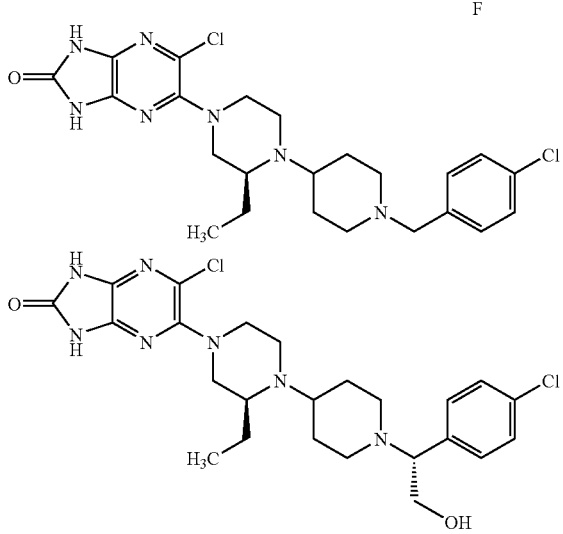
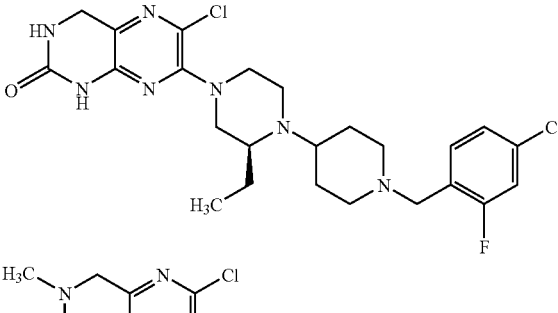
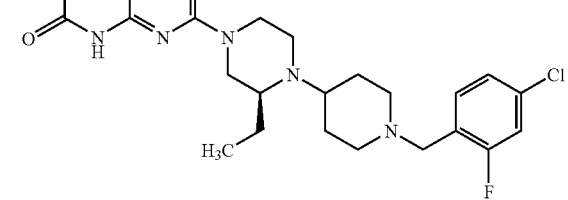
and
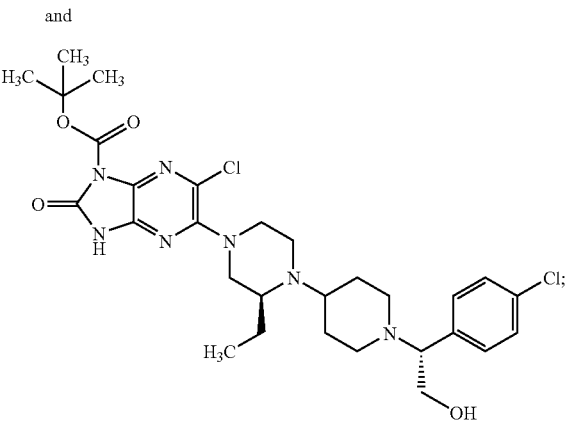
or a pharmaceutically acceptable salt thereof.

3. A compound according to claim 1, selected from the group consisting of:

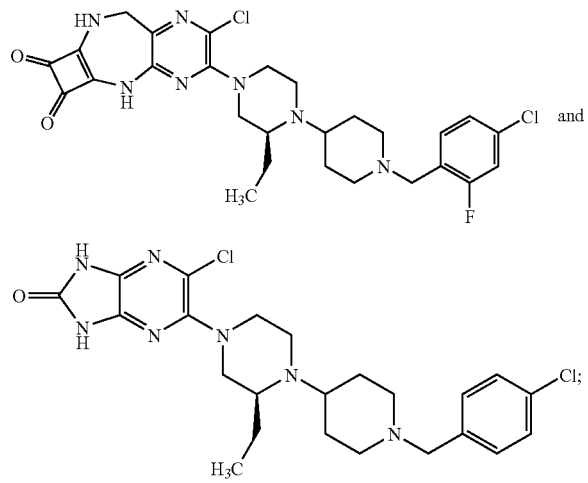

or a pharmaceutically acceptable salt thereof.

4. A pharmaceutical composition comprising at least one compound of claim 1, or a pharmaceutically acceptable salt thereof, in combination with at least one pharmaceutically acceptable carrier.

5. The pharmaceutical composition of claim 4, further comprising at least one additional agent, drug, medicament, antibody and/or inhibitor for treating a CXCR3 chemokine receptor mediated disease.

6. A pharmaceutical composition comprising at least one compound of claim 2, or a pharmaceutically acceptable salt thereof, in combination with at least one pharmaceutically acceptable carrier.

7. The pharmaceutical composition of claim 6, further comprising at least one additional agent, drug, medicament, antibody and/or inhibitor for treating a CXCR3 chemokine receptor mediated disease.

* * * * *